(12) United States Patent
Schmidt et al.

(10) Patent No.: US 11,951,302 B2
(45) Date of Patent: *Apr. 9, 2024

(54) NERVE CUFF ELECTRODES FABRICATED USING OVER-MOLDED LCP SUBSTRATES

(71) Applicant: THE ALFRED E. MANN FOUNDATION FOR SCIENTIFIC RESEARCH, Valencia, CA (US)

(72) Inventors: Siegmar Schmidt, Simi Valley, CA (US); Boon Khai Ng, La Crescenta, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 17/807,370

(22) Filed: Jun. 16, 2022

(65) Prior Publication Data
US 2022/0323748 A1    Oct. 13, 2022

Related U.S. Application Data

(63) Continuation of application No. 16/430,785, filed on Jun. 4, 2019, now Pat. No. 11,794,003, which is a
(Continued)

(51) Int. Cl.
*A61N 1/05* (2006.01)
*A61N 1/36* (2006.01)
(Continued)

(52) U.S. Cl.
CPC ......... *A61N 1/0556* (2013.01); *A61N 1/3752* (2013.01); *A61B 5/389* (2021.01);
(Continued)

(58) Field of Classification Search
None
See application file for complete search history.

(56) References Cited

U.S. PATENT DOCUMENTS 5,251,634 A    10/1993 Weinberg
6,210,339 B1   4/2001 Kiepen et al.
(Continued)

FOREIGN PATENT DOCUMENTS

WO   WO2009045772    4/2009
WO   WO20120154256   11/2012

OTHER PUBLICATIONS

U.S. Appl. No. 17/807,349 (Year: 2022).*
(Continued)

*Primary Examiner* — Catherine M Voorhees
*Assistant Examiner* — Elizabeth K So
(74) *Attorney, Agent, or Firm* — Michael J. Bolan; Vista IP Law Group, LLP

(57) ABSTRACT

An electrode lead may comprise a flexible circuit that includes a planar dielectric substrate including an elongated lead substrate portion having opposing ends, an electrode carrying substrate portion disposed on one end of the lead substrate portion, and a connector substrate portion disposed on the other end of the lead substrate portion, wherein the lead substrate portion is pre-shaped into a three-dimensional structure. The flexible circuit may further include an electrically conductive trace extending from the connector substrate portion to the electrode carrying substrate portion, a first window formed in the connector substrate portion to expose the electrically conductive trace to form a connector pad, and a second window formed in the electrode carrying substrate portion to expose the electrically conductive trace
(Continued)

to form an electrode pad. The electrode lead may further comprise a lead connector that incorporates the connector substrate portion.

15 Claims, 23 Drawing Sheets

Related U.S. Application Data continuation of application No. 15/634,134, filed on Jun. 27, 2017, now abandoned.

(60) Provisional application No. 62/415,028, filed on Oct. 31, 2016.

(51) Int. Cl.
   *A61N 1/375* (2006.01)
   *A61B 5/389* (2021.01)

(52) U.S. Cl.
   CPC .......... *A61N 1/0558* (2013.01); *A61N 1/3605* (2013.01); *A61N 1/375* (2013.01)

(56) References Cited

U.S. PATENT DOCUMENTS

| | | |
|---|---|---|
| 7,794,256 B1 | 9/2010 | Sochor |
| 8,792,973 B2 | 7/2014 | Moran |
| 9,549,708 B2 | 1/2017 | Mercanzini |
| 9,889,304 B2 | 2/2018 | Mercanzini |
| 11,794,003 B2 * | 10/2023 | Schmidt .............. A61N 1/0556 |
| 2002/0198582 A1 | 12/2002 | Edell |
| 2005/0070982 A1 | 3/2005 | Heruth |
| 2005/0186829 A1 | 8/2005 | Balsells |
| 2006/0030919 A1 | 2/2006 | Mrva et al. |
| 2007/0123765 A1 | 5/2007 | Hetke |
| 2009/0132042 A1 | 5/2009 | Hetke |
| 2011/0066196 A1 | 3/2011 | Alexander |
| 2011/0154655 A1 | 6/2011 | Hetke |
| 2011/0251473 A1 | 10/2011 | Moran |
| 2011/0301665 A1 | 12/2011 | Mercanzini |
| 2012/0150255 A1 | 6/2012 | Lindenthaler |
| 2012/0316417 A1 | 12/2012 | Vetter |
| 2013/0030352 A1 | 1/2013 | Seymour |
| 2013/0085361 A1 | 4/2013 | Mercanzini |
| 2013/0090711 A1 | 4/2013 | Ramachandran |
| 2013/0150938 A1 | 6/2013 | Carbunaru |
| 2013/0304174 A1 | 11/2013 | Langhals |
| 2014/0005763 A1 | 1/2014 | Cederna |
| 2014/0058482 A1 | 2/2014 | Gupta et al. |
| 2014/0163659 A1 | 6/2014 | Boling |
| 2014/0303703 A1 | 10/2014 | Mercanzini |
| 2015/0119673 A1 | 4/2015 | Pellinen |
| 2015/0128413 A1 | 5/2015 | Vetter |
| 2015/0157854 A1 | 6/2015 | Hetke |
| 2016/0287863 A1 | 10/2016 | Mercanzini |
| 2016/0331326 A1 | 11/2016 | Xiang |
| 2016/0331994 A1 | 11/2016 | Smith |
| 2017/0266436 A1 | 9/2017 | Suwito |

OTHER PUBLICATIONS

Annex to Form PCT/ISA/206 Communication Relating to the Results of the Partial International Search dated Oct. 9, 2017 in International Application No. PCT/US2017/039424 (2pages).

PCT International Search Report for PCT/US2017/039424, Applicant: The Alfred E. Mann Foundation for Scientific Research, Form PCT/ISA/210 and 220, dated Mar. 1, 2018 (9 pages).

PCT Written Opinion of the International Search Authority for PCT/US2017/039424, Applicant: The Alfred E. Mann Foundation for Scientific Research, Form PCT/ISA/237, dated Mar. 1, 2018 (12 pages).

PCT International Preliminary Report on Patentability for PCT/US2017/039424, Applicant: The Alfred E. Mann Foundation for Scientific Research, Form PCT/IB/373, dated Apr. 30, 2019 (14 pages).

* cited by examiner

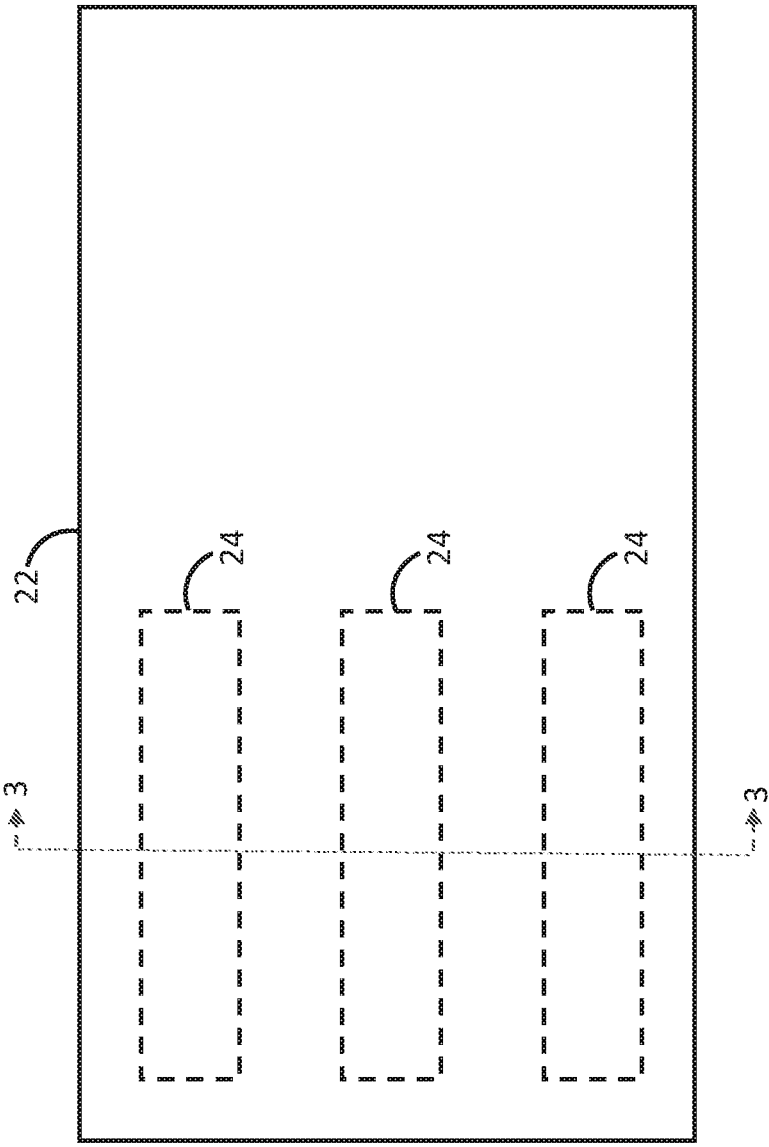
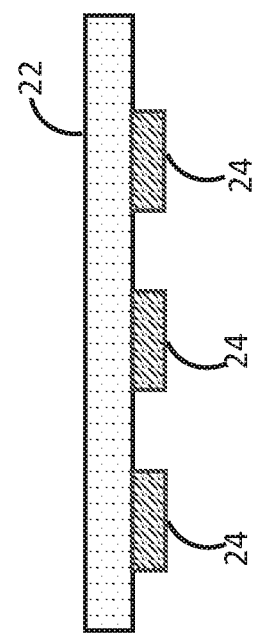
Fig. 2
Fig. 3

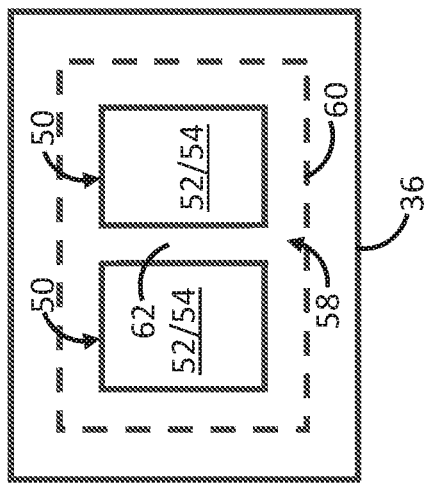
Fig. 7a  Fig. 7b  Fig. 7c
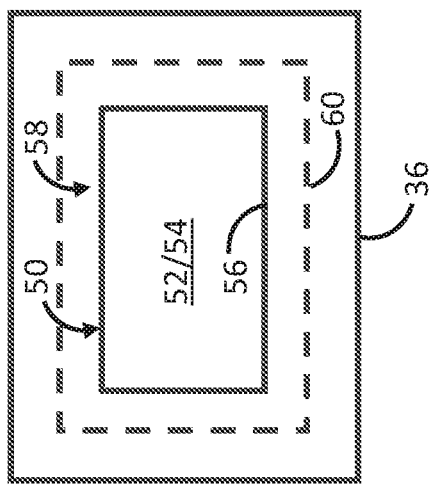
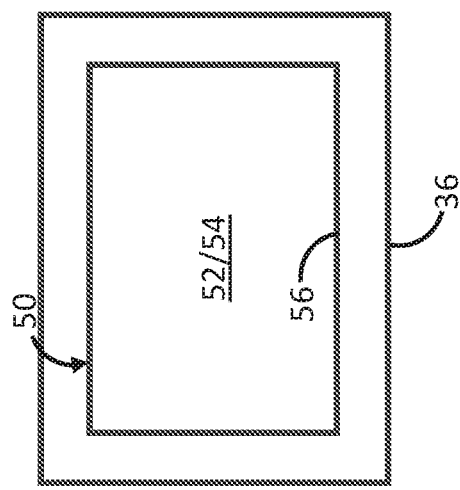
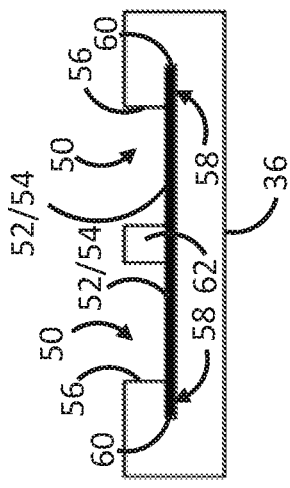
Fig. 8a  Fig. 8b  Fig. 8c
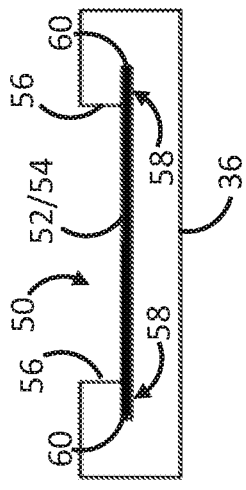
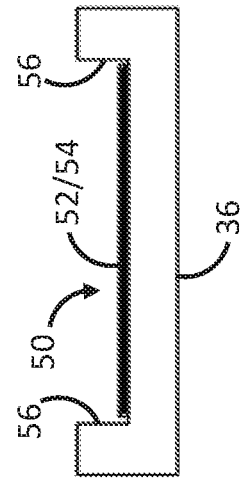

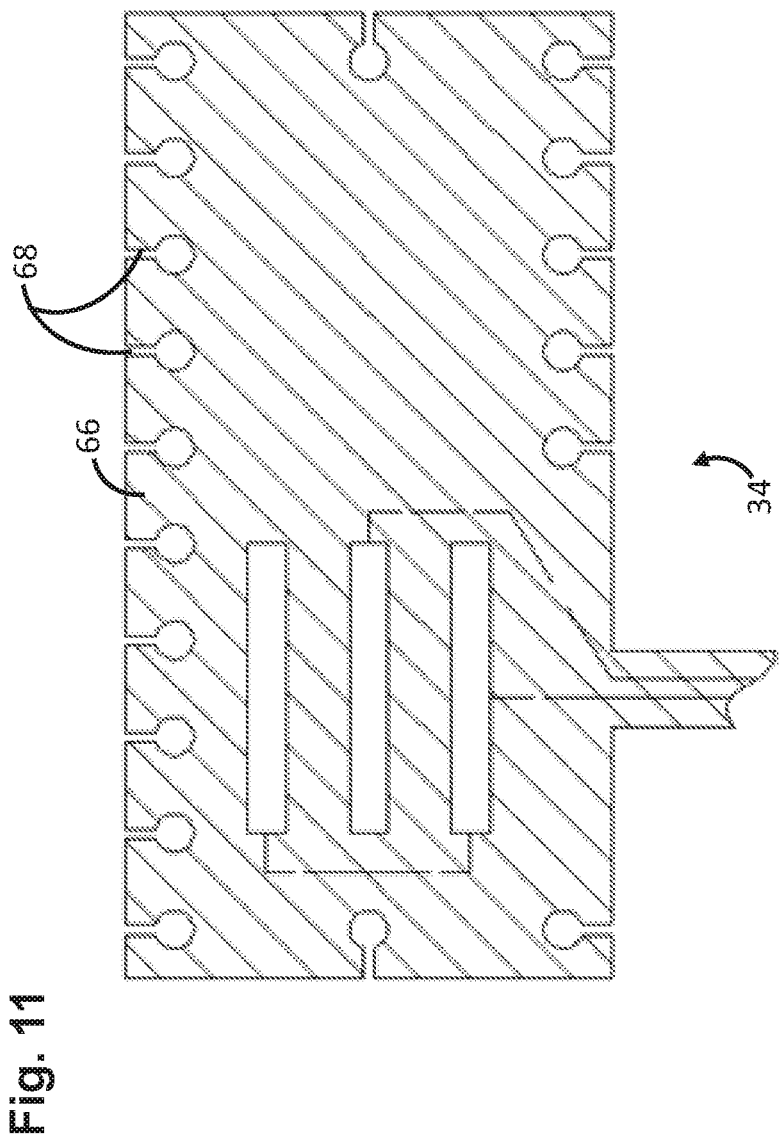

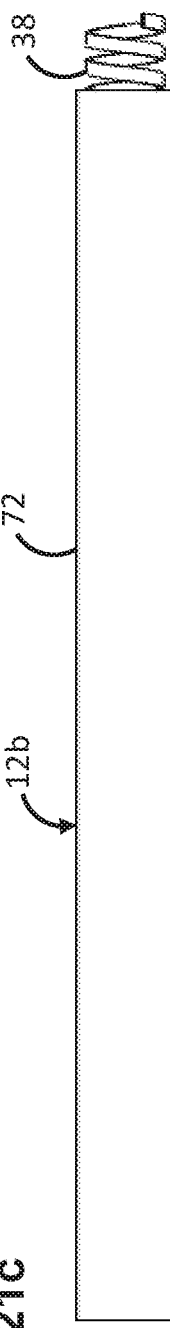

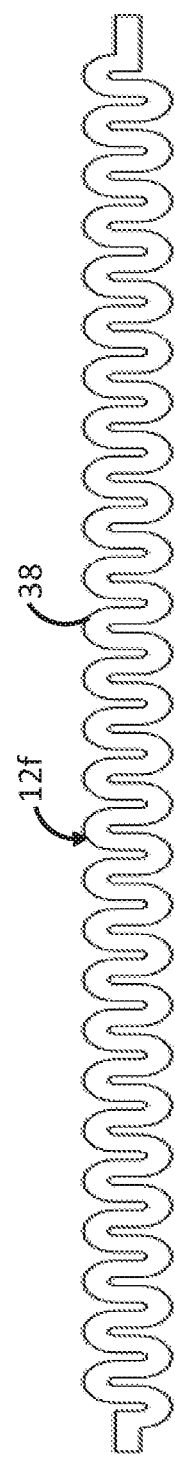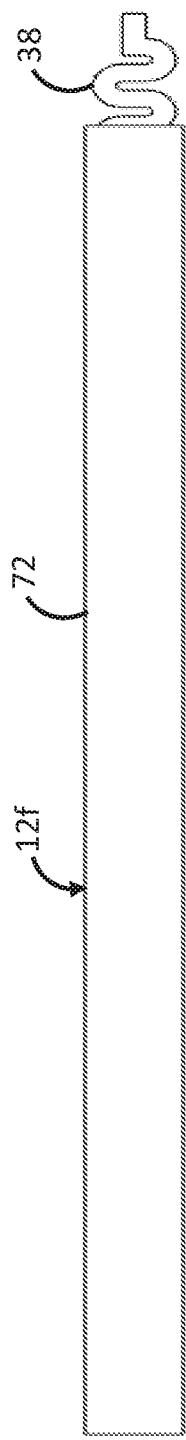

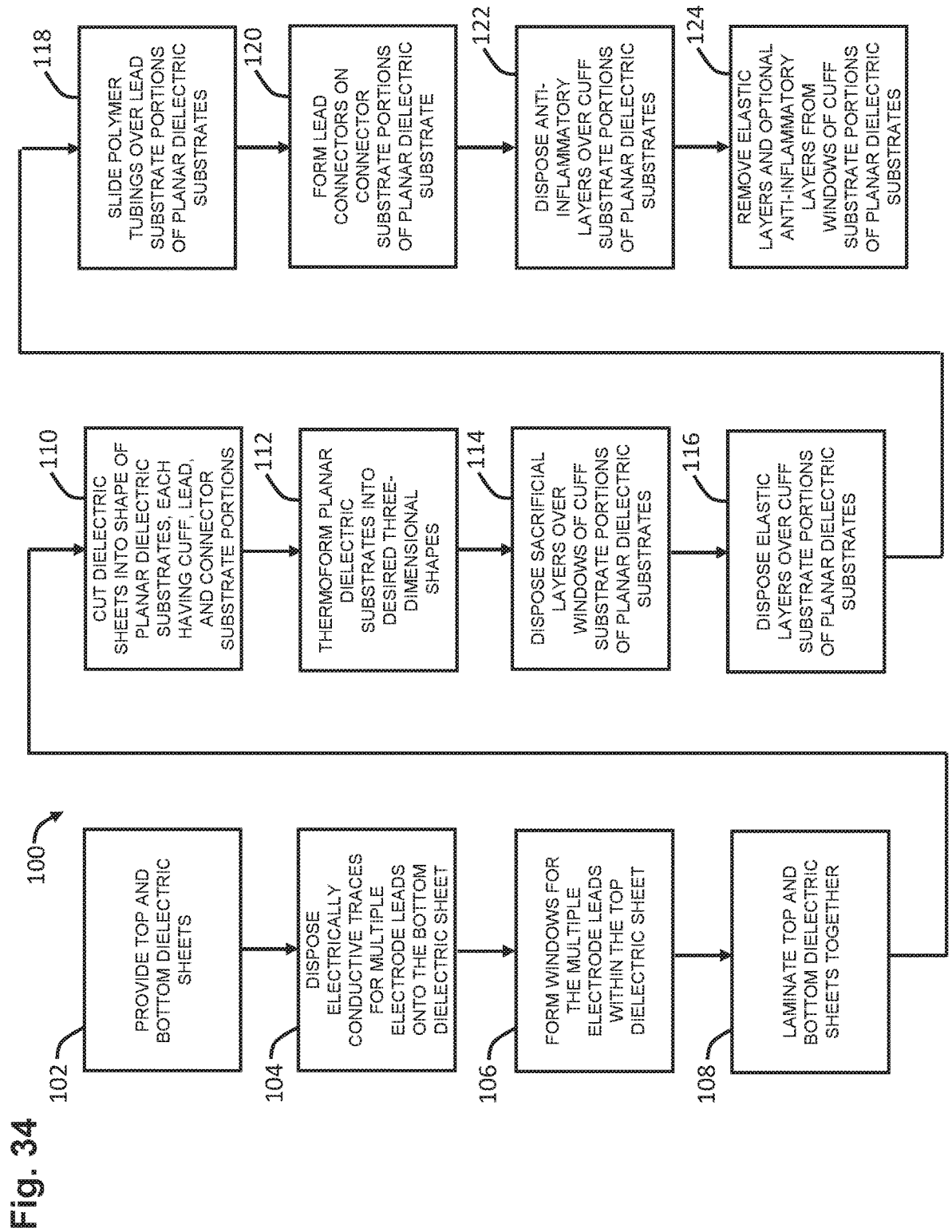

NERVE CUFF ELECTRODES FABRICATED USING OVER-MOLDED LCP SUBSTRATES

RELATED APPLICATION

The present application is a continuation of U.S. patent application Ser. No. 16/430,785, filed Jun. 4, 2019 (U.S. Patent Publication No. 2019/0282805) (now U.S. Pat. No. 11,794,003), which is a continuation of U.S. patent application Ser. No. 15/634,134, filed Jun. 27, 2017 (U.S. Patent Publication No. 2018/0117313) (now abandoned), which claims the benefit of U.S. Provisional Patent Application Ser. No. 62/415,028, filed Oct. 31, 2016. The contents of the aforementioned patent applications are hereby expressly incorporated by reference in their entirety.

FIELD OF THE INVENTION

The present invention generally relates to implantable neurostimulation leads, and specifically relates to implantable nerve cuff electrodes that can be used to stimulate nerves.

BACKGROUND OF THE INVENTION

Nerve cuff electrodes are conventionally manufactured using implantable grade silicone or, in some cases, polyurethane. Nerve cuff electrodes generally comprise a lead body, a connector proximally located on the lead body, a cuff body distally located on the lead body, electrode contacts placed on the inner surface of the cuff body, and electrical conductors extending from the cuff body through the lead body to the connector. The method of making these nerve cuffs electrodes is typically time consuming, since the conductors and electrode contacts in the cuff body are overmolded using molds. The electrode contacts must be connected to the ends of the conductors using a mechanical crimp or welded together. The cuff body is conventionally formed by injection molding the silicone over the conductors and part of the electrode contact. The lead body that contains the conductors is overmolded with insulative material such as silicone or polyurethane. This entire process for making a nerve cuff electrode is time and labor intensive and therefore adds to the final cost of the finished lead with nerve cuff electrode.

It is desirable to make nerve cuff electrodes that would be less labor intensive and easier to make. The substrate material used to make the nerve cuff electrode should be inert in biological environments, and mechanically flexible, substantially impermeable to moisture, oxygen, and other gases and liquids, be relatively low cost, and have suitable dielectric properties. A new class of material, known as thermoplastic liquid crystal polymers (LCP), satisfies these unique combination of properties and is well suited for cuff electrodes as a substrate on which the electrical circuitry is disposed. LCPs offer the additional advantage of precision molding and being amenable to photolithography and thin-film deposition of electrical circuitry, which can greatly reduce the time and labor to manufacture the cuff electrode.

The planarity of the LCP substrates provides various opportunities for incorporating beneficial features that are not otherwise available to conventional lead structures. However, due to its planar nature, the use of LCP as a substrate in nerve cuff electrodes, and medical leads in general, provides several challenges. First, as discussed above, it is important that medical leads be flexible in all planes, especially when implanted in regions of the body prone to extensive movement, such as the neck region, of a patient. Although an LCP substrate may be flexible in one plane perpendicular to its surface, the same LCP substrate may be somewhat rigid in the plane along its surface. Second, the lead ports for conventional neurostimulation devices are generally cylindrical, thereby making the mechanical and electrical transition from planar LCP-based leads to such neurostimulation devices particularly challenging. Third, because the edges of LCP substrates tend to be sharp, such LCP substrates may need to be over-molded with a softer material, such as silicone. However, because there are only two sides of the LCP substrate on which the silicone can be adhered to, the silicone may be prone to delamination from the LCP substrate. Additionally, for the same reason, electrodes disposed on one of these planar surfaces of the LCP substrate may also be prone to delamination from the LCP substrate.

There, thus, remains a need for providing improvements to medical leads, such as nerve cuff electrodes, that utilize planar dielectric substrates, such as LCP, on which electrical circuitry is disposed.

SUMMARY OF THE INVENTION

In accordance with the present inventions, electrode leads are provided. Such electrode leads may comprise an elongated lead body, a lead connector disposed at a proximal end of the lead body (e.g., one that can be inserted into a corresponding connector of a neurostimulator), an electrode carrying structure disposed at a distal end of the lead body, at least one connector contact carried by the lead connector, at least one electrode contact (e.g., three electrode contacts in a tripolar electrode arrangement) carried by the electrode carrying structure, and at least one electrical conductor extending through the lead body between the at least one connector contact and the at least one electrode contact.

In one embodiment, the lead body, electrode carrying structure, and/or lead connector are planar. In this case, the lead body, electrode carrying structure, and/or lead connector may comprise a planar dielectric substrate (e.g., liquid crystal polymer (LCP)). As one example, the electrode carrying structure may comprise a biologically compatible, elastic, electrically insulative cuff body affixed to the distal end of the lead body, and being configured for being circumferentially disposed around a nerve. The electrode contact(s) may be configured for being on an inner surface of the cuff body when circumferentially disposed around a nerve. As another example, the electrode carrying structure may comprise a biologically compatible, elastic, electrically insulative paddle body affixed to the distal end of the lead body. Such lead bodies may comprise an outer layer of insulative material composed of one of silicone, polyurethane, polyether polyurethane, polycarbonate polyurethane, parylene, perfluoroalkoxy alkanes (PFA), and polytetrafluoroethylene (PTFE).

In accordance with the present inventions, flexible circuits are also provided. Such flexible circuits may comprise a planar dielectric substrate (e.g., liquid crystal polymer (LCP)) including an elongated lead substrate portion having opposing ends, an electrode carrying substrate portion disposed on one end of the lead substrate portion, and a connector substrate portion disposed on the other end of the lead substrate portion. Such flexible circuits may also comprise an electrically conductive trace extending from the connector substrate portion to the electrode carrying substrate portion, at least a first window is formed in the connector substrate portion to expose the electrically conductive trace to form a connector pad, and at least a second window is formed in the electrode carrying substrate portion to expose the electrically conductive trace to form an electrode pad.

In one embodiment, the electrode carrying substrate portion is an enlarged cuff substrate portion pre-shaped into a cuff sized for being circumferentially disposed around a nerve. The cuff substrate portion may be, e.g., rectangular. The electrode pad may, e.g., be configured for facing a nerve when the cuff substrate portion is circumferentially disposed around a nerve. In another embodiment, the electrode carrying substrate portion is an enlarged paddle substrate portion. Such flexible circuits may further comprise an outer layer of insulative material (e.g., one of silicone, polyurethane, polyether polyurethane, polycarbonate polyurethane, parylene, perfluoroalkoxy alkanes (PFA), and polytetrafluoroethylene (PTFE)) disposed over the planar dielectric substrate.

In accordance with the present inventions, lead connectors (e.g., those that can be inserted into corresponding connectors of neurostimulators) are also provided. Such lead connectors may comprise a planar dielectric connector substrate (e.g., one composed of liquid crystal polymer (LCP)), and at least one connector pad carried by the connector substrate. Such lead connectors may further comprise at least one electrically conductive trace disposed within the connector substrate, and at least one window formed in the connector substrate to expose the electrically conductive trace(s) to form the connector pad(s).

In accordance with a first aspect of the present inventions, the elongated planar lead body of an electrode lead or the lead substrate portion of a flexible circuit is pre-shaped into a three-dimensional structure (e.g., a helical structure or a sigmoid structure).

In accordance with a second aspect of the present inventions, the elongated planar lead body of an electrode lead has at least one slit to form a plurality of planar strands, in which case, electrical conductors will extend within the plurality of strands between the connector contact(s) and the electrode contact(s). In one embodiment, the slit(s) may extend through the distal end of the lead body, such that the planar strands have loose ends. The planar strands may be pre-shaped into three-dimensional structures (e.g., helical structures, which may form a co-helical structure, or sigmoid structures). Electrode contacts may be respectively affixed to the loose ends of the planar strands. In another embodiment, the slit(s) may not extend through either the proximal end or the distal end of the lead body, such that both ends of the lead body are intact. The slit(s) may comprise a plurality of collinear slits, such that the lead body is intact between the collinear slits.

Similarly, the lead substrate portion of a flexible circuit has at least one slit to form a plurality of planar strands, in which case, the electrically conductive traces respectively extend through the planar strands. In one embodiment, the slit(s) may extend through one end of the lead substrate portion, such that the planar strands have loose ends. In this case, a plurality of electrode carrying substrate portions may be respectively disposed on the loose ends of the planar strands, with the second plurality of windows being respectively formed in the electrode carrying substrate portions. The planar strands may be pre-shaped into three-dimensional structures (e.g., helical structures, which may form a co-helical structure, or sigmoid structures). In another embodiment, the slit(s) may not extend through either of the opposing ends of the lead substrate portion, such that both ends of the lead substrate portion are intact. In this case, a single electrode carrying substrate portion may be disposed at the one end of the lead substrate portion. The slit(s) may comprise a plurality of collinear slits, such that the lead substrate portion is intact between the collinear slits.

In accordance with a third aspect of the present inventions, a plurality of first windows are formed in one of the connector substrate portion and the electrode carrying substrate portion to expose the electrically conductive trace to form a respective connector pad or electrode pad, such that the respective connector pad or electrode pad has a peripheral region and an interior region embedded within the planar dielectric substrate. In one embodiment, the interior region is smaller than the size of each of the first windows.

In accordance with a fourth aspect of the present inventions, the periphery of the planar electrode carrying structure of an electrode lead has a plurality of open slots (e.g., a slotted hole, a rounded slot, or a slotted "T"), and an outer layer of insulative material covers the electrode carrying structure over the open slots. Similarly, periphery of the electrode carrying structure of a flexible circuit has a plurality of open slots (e.g., a slotted hole, a rounded slot, or a slotted "T"), and an outer layer of insulative material covering the electrode carrying substrate portion over the open slots.

In accordance with a fifth aspect of the present inventions, an electrode lead comprises an elongated planar main lead body having a proximal end and a distal end, and an elongated planar branch lead body extending from the main lead body between the proximal end and distal end. In this case, the lead connector disposed at the proximal end of the main lead body, the electrode carrying structure is disposed at the distal end of the main lead body, a plurality of connector contacts are carried by the lead connector, at least one first electrode contact is carried by the electrode carrying structure, at least one second electrode contact is carried by the branch lead body, and a plurality of electrical conductors extend through the main lead body between the plurality of connector contacts and the plurality of electrode contacts. In embodiment, the branch lead body has a barb.

Similarly, the planar dielectric substrate of a flexible circuit includes an elongated main lead substrate portion having opposing ends, at least one electrode carrying substrate portion disposed on one end of the main lead substrate portion, a connector substrate portion disposed on the other end of the main lead substrate portion, and an elongated branch lead substrate portion extending from the main lead substrate portion between the opposing ends. In this case, the flexible circuit may comprise a first electrically conductive trace extending from the connector substrate portion to the electrode carrying substrate portion, a second electrically conductive trace extending from the connector substrate portion to the branch lead substrate portion, first and second windows formed in the connector substrate portion to expose the first and second electrically conductive traces to respectively form first and second connector pads, a third window formed in the electrode carrying portion to expose the first electrically conductive trace to form a first electrode pad, and a fourth window formed in the branch lead substrate portion to expose the second electrically conductive trace to form a second electrode pad. In one embodiment, the elongated branch lead substrate portion has a barb.

In accordance with a sixth aspect of the present inventions, an electrode lead comprises a plurality of biologically compatible, elastic, electrically insulative cuff bodies affixed to the distal end of the lead body. In this case, the electrode lead comprises a plurality of connector contacts carried by the lead connector, a plurality of electrode contacts respectively carried by the plurality of cuff bodies, and a plurality of electrical conductors extending within the lead body between the plurality of connector contacts and the plurality of electrode contacts. The lead body may be divided into proximal lead body portion and a distal lead body portion, the cuff bodies may comprise a proximal cuff body and a distal cuff body, the proximal lead body portion may extend between the lead connector and the proximal cuff body, and the distal lead body portion may extend between the proximal cuff body and the distal cuff body.

Similarly, a flexible circuit comprises first and second enlarged cuff substrate portions disposed on one end of the lead substrate portion. In this case, the flexible circuit comprise first and second electrically conductive traces respectively extending from the connector substrate portion to the first and second cuff substrate portions, first and second windows formed in the connector substrate portion to expose the first and second electrically conductive traces to respectively form first and second connector pads, and third and fourth windows formed in the first and second cuff substrate portions to expose the first and second electrically conductive traces to respectively form first and second electrode pads. The lead substrate portion may be divided into a first lead substrate portion and a second lead substrate portion, the first lead substrate portion may extend between the connector substrate portion and first cuff substrate portion, and the second lead substrate portion may extend between the first cuff substrate portion and the second cuff substrate portion.

In accordance with an eighth aspect of the present inventions, the cuff body is pre-shaped to curve in two orthogonal directions, such that the cuff body has a bi-stable structure. The cuff body may be configured between an unfurled stable state and a furled stable state. Similarly, the enlarged cuff substrate portion of a flexible circuit is pre-shaped to curve in two orthogonal directions, such that the cuff substrate portion has a bi-stable structure. The cuff substrate portion may be configured for being configured between an unfurled stable state and a furled stable state.

In accordance with an eighth aspect of the present inventions, the lead connector of an electrode lead includes a rigid cylindrical rod having an outer surface on which the connector substrate is affixed, such that connector contact(s) faces outward away from the cylindrical rod. The connector substrate may be pre-shaped to conform to the outer surface of the cylindrical rod. Similarly, an electrode lead may include the flexible circuit, and the rigid cylindrical rod on which the connector substrate portion of the flexible circuit is affixed, such that the connector pad faces outward away from the cylindrical rod to form a lead connector contact. The connector substrate may be pre-shaped to conform to the outer surface of the cylindrical rod. Similarly, a lead connector may comprise a rigid cylindrical rod on which the connector substrate is affixed, such that the connector pad(s) faces outward away from the cylindrical rod to form the lead connector contact. The connector substrate may be pre-shaped to conform to the outer surface of the cylindrical rod.

In accordance with a ninth aspect of the present invention, the lead connector of an electrode lead comprises at least one rigid connector contact having an arcuate surface affixed to the connector substrate and electrically coupled respectively to the connector pad(s), and a cylindrical, rigid, electrical insulator at least partially encapsulating the connector substrate and the connector contact(s), such that only the arcuate surface of each of the connector contact(s) is exposed. Similarly, the electrode lead may comprise a connector contact having an arcuate surface affixed to the connector substrate portion of the flexible circuit and electrically coupled respectively to the connector pad, and a cylindrical, rigid, electrical insulator at least partially encapsulating the connector substrate portion and the connector contact, such that only the arcuate surface of the connector contact is exposed. Similarly, a lead connector may comprise at least one rigid connector contact having an arcuate surface affixed to the connector substrate and electrically coupled respectively to the at least one connector pad, and a cylindrical, rigid, electrical insulator at least partially encapsulating the connector substrate and the at least one connector contact, such that only the arcuate surface of each of the at least one connector contact is exposed.

The electrical insulator may be composed of, e.g., epoxy or polyurethane. The arcuate surface of each of the connector contact(s) may conform with an outer surface of the electrical insulator. In one embodiment, each of the connector contact(s) has an arc length of 180 degrees or less. In another embodiment, each of the connector contact(s) has an arc length greater than 180 degrees. Each of the connector contact(s) may be, e.g., disk-shaped or half-moon shaped. Each of the connector contact(s) may have a notch in which the connector substrate is disposed.

In accordance with a tenth aspect of the present invention, the lead connector of an electrode lead comprises a cylindrical connector portion having at least one connector contact, at least one wire respectively coupled between the connector pad(s) and the connector contact(s), and a cylindrical, rigid, electrical insulator encapsulating the connector substrate. Similarly, an electrode lead may comprise a cylindrical connector portion having a connector contact, at least one wire coupled between the connector pad and the connector contact, and a cylindrical, rigid, electrical insulator encapsulating the connector substrate portion of a flexible circuit. Similarly, a lead connector may comprise a cylindrical connector portion having at least one connector contact, at least one wire respectively coupled between the connector pad(s) and the connector contact(s), and a cylindrical, rigid, electrical insulator encapsulating the connector substrate portion. The electrical insulator may be composed of, e.g., epoxy or polyurethane. In one embodiment, each of the connector contact(s) is a ring contact. In another embodiment, the wire(s) extends longitudinally along the cylindrical connector portion from the connector contact(s) out of a distal face of the cylindrical connector portion.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which:

FIG. 2 is a plan view of a cuff electrode of the electrode lead of FIG. 1, which can be rolled up and circumferentially disposed around a nerve;

FIG. 3 is a cross-sectional view of the cuff electrode of FIG. 2, taken along the line 3-3;

FIG. 6a is a cross-sectional view of the flexible circuit showing one embodiment of an arrangement of electrically conductive traces, taken along the line 6a-6a;

FIG. 7a is a plan view of one connector pad or electrode pad of the flexible circuit of FIG. 5, wherein no portion of the connector pad or electrode pad is embedded within a planar dielectric substrate;

FIG. 7b is a plan view of one connector pad or electrode pad of the flexible circuit of FIG. 5, wherein the peripheral region of the connector pad or electrode pad is embedded within a planar dielectric substrate;

FIG. 7c is a plan view of one connector pad or electrode pad of the flexible circuit of FIG. 5, wherein the peripheral region and interior region of the connector pad or electrode pad is embedded within a planar dielectric substrate;

FIG. 8a is a cross-sectional view of the connector pad or electrode pad of FIG. 7a;

FIG. 8b is a cross-sectional view of the connector pad or electrode pad of FIG. 7b;

FIG. 8c is a cross-sectional view of the connector pad or electrode pad of FIG. 7c;

FIG. 11 is a plan view of one embodiment of a cuff substrate portion of the flexible circuit of FIG. 5, particularly showing an anti-inflammatory coating disposed over the cuff substrate portion;

FIG. 21a is a plan view of one embodiment of a lead body of the electrode lead of FIG. 1;

FIG. 21b is a plan view of another embodiment of a lead body of the electrode lead of FIG. 1;

FIG. 21c is a plan view of the lead body of FIG. 21b with an additional insulating tube;

FIG. 21h is a plan view of yet another embodiment of a lead body of the electrode lead of FIG. 1;

FIG. 21i is a plan view of the lead body of FIG. 21h with an additional insulating tube;

FIG. 34 is a flow diagram illustrating one method of constructing an electrode lead in accordance with various embodiments of the present invention.

DETAILED DESCRIPTION OF THE EMBODIMENTS

Figure 1:
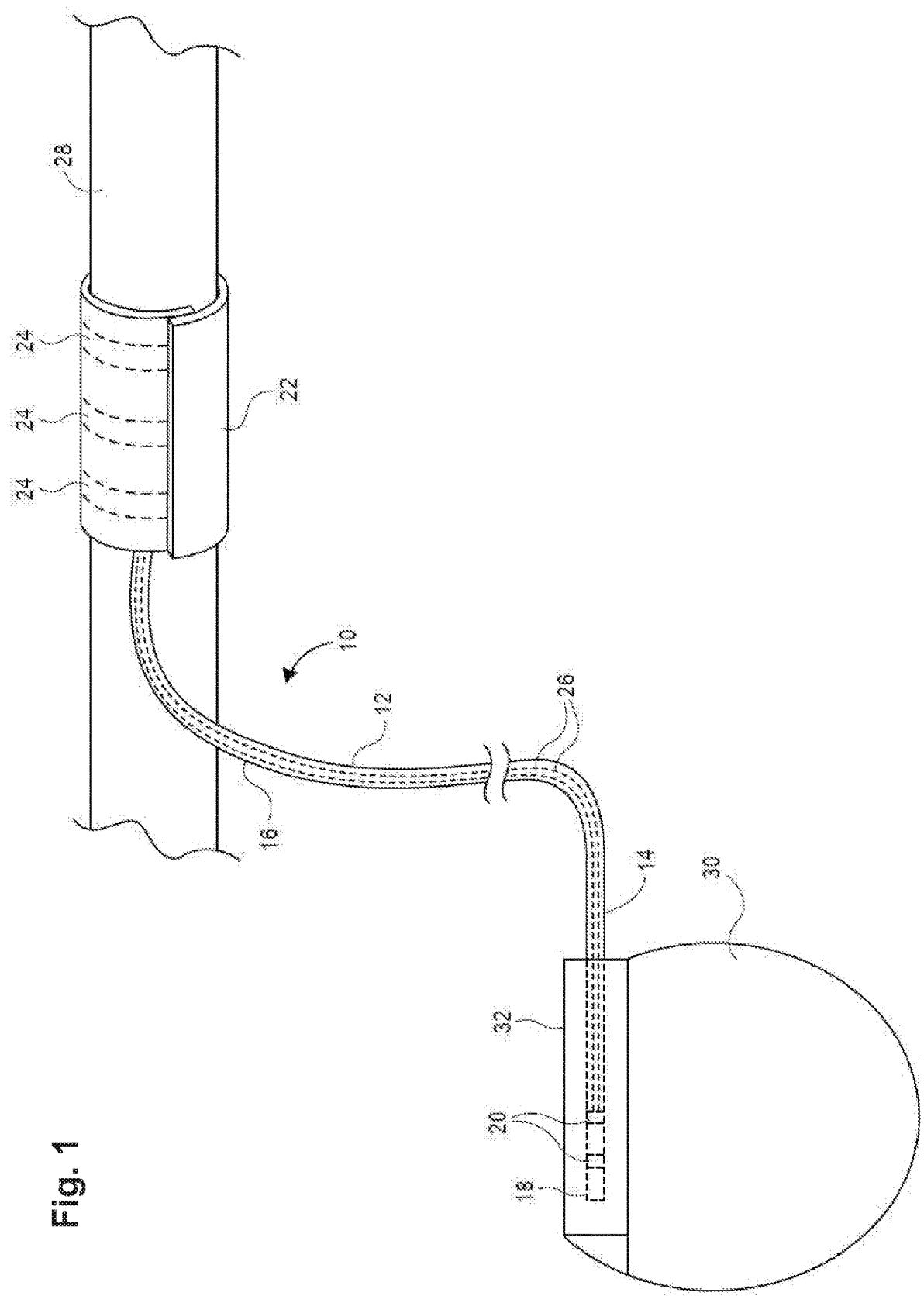
FIG. 1 is a perspective view of an electrode lead constructed in accordance with one embodiment of the present invention, wherein a cuff body of the electrode lead is particularly shown disposed on a nerve.

Referring first to FIGS. 1-3, an electrode lead 10 constructed in accordance with one embodiment of the present inventions will now be described. The electrode lead 10 may be used for any medical treatment where it is desired to stimulate a nerve and/or record physiological signals from a nerve or surrounding tissue.

The electrode lead 10 generally comprises an elongated planar lead body 12 having a proximal end 14 and a distal end 16, a lead connector 18 affixed to the proximal end 14 of the lead body 12, at least one lead connector contact 20 (two shown) disposed on the lead connector 18, a planar electrode carrying structure 22 affixed to the distal end 16 of the lead body 12, at least one electrode contact 24 (three shown in phantom in FIG. 1) disposed on the electrode carrying structure 22, and at least one electrical conductor 26 (two shown) extending through the lead body 12 between the lead connector contacts 20 and the electrode contacts 24. For the purposes of this specification, "planar" means having a two-dimensional characteristic, with the thickness of the body being much less than the width of the body. For example, the width of the body may be greater than ten times, greater than fifty times, or even greater than one hundred times the width of the body.

In the illustrated embodiment, the electrode carrying structure 22 takes the form of a cuff body 22 that can be circumferentially disposed around tissue, e.g., a nerve 28, such that the electrode contacts 24 are disposed on an inner surface of the cuff body 22 in contact with the nerve 28. In alternative embodiments, the electrode carrying structure 22 can be any structure suitable for carrying the electrode contacts 24, e.g., a paddle or even the distal end of the lead body 12.

In the illustrated embodiment, the electrode contacts 24 can be in the form of a guarded tripolar electrode arrangement (e.g., anode-cathode-anode) that can be used for purposes of stimulating the nerve 28. Two of the outer electrode contacts 24 (the anodes) can be ganged together and coupled to one of the lead connector contacts 18 via an electrical conductor 26, and the remaining electrode contact 24 (the middle cathode) may be coupled to the other lead connector contact 18 via the other electrical conductor 26. It should be appreciated that, alternatively, the number of electrode contacts 24, lead connector contacts 18, and electrical conductors 26 can be identical, such that electrode contacts 24 may be energized independently of each other.

The cuff body 22 is relatively thin, e.g., having a thickness less than 1 mm, and preferably less than 0.5 mm, so that the cuff body 22 may be easily disposed around in conformance with the nerve 28. The cuff body 22 takes the form of a planar sheet (as best shown in FIG. 2) that can be rolled up on itself to be circumferentially disposed around the nerve 28 (as best shown in FIG. 1). The electrode lead 10 may comprise a strap and buckle arrangement, along with a locking mechanism, that tightens and secures the cuff body 22 around the nerve 28, as described in U.S. Provisional Patent Application Ser. No. 62/500,080, entitled "Nerve Cuff Electrode Locking Mechanism," which is expressly incorporated herein by reference.

To this end, the lead connector 18 (which is a male connector in the illustrated embodiment) can be inserted into a corresponding female connector 32 of a neurostimulation device 30, which supplies electrical pulses to the electrode contacts 24 of the electrode lead 10 in accordance with a stimulation regimen. In embodiments described herein, the female connector 32 of the neurostimulation device 30 is conventional in nature. For example, the female connector 32 may take the form of an in-line connector, such as a Bal Seal® connector.

Recording electrode contacts can also be connected to the neurostimulation device 30 to provide sensed physiological signals (e.g., electromyogram (EMG) signals) to the neurostimulation device 30, and thus, in an alternative embodiment, the electrode contacts 24 of the electrode lead 10 may serve as recording electrodes. Alternatively, the recording electrode may be on a separate lead body, which is connected to the neurostimulation device 30.

Figure 4:
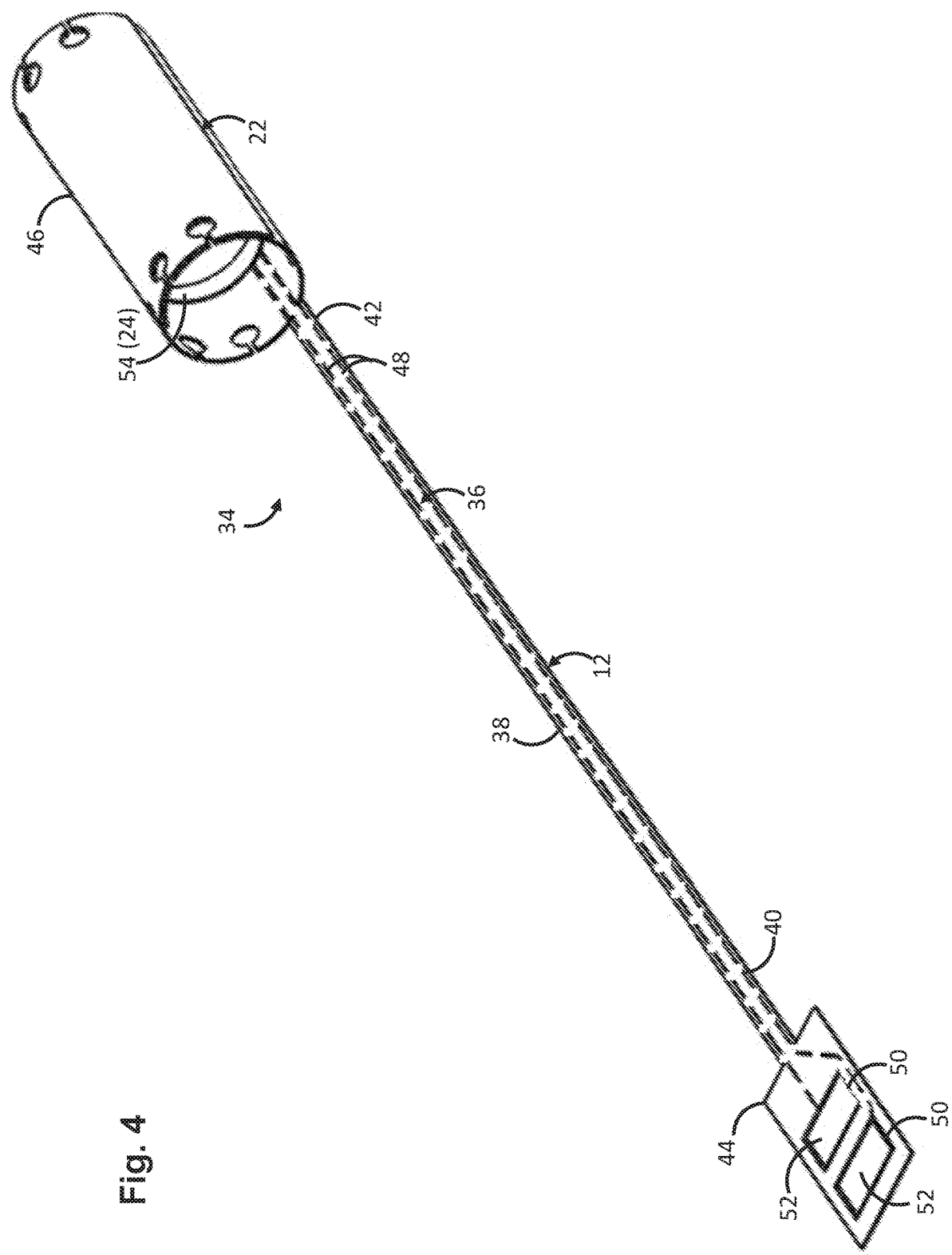
FIG. 4 is a perspective view of one embodiment of a flexible circuit that can form a portion of the electrode lead of FIG. 1.
Figure 5:
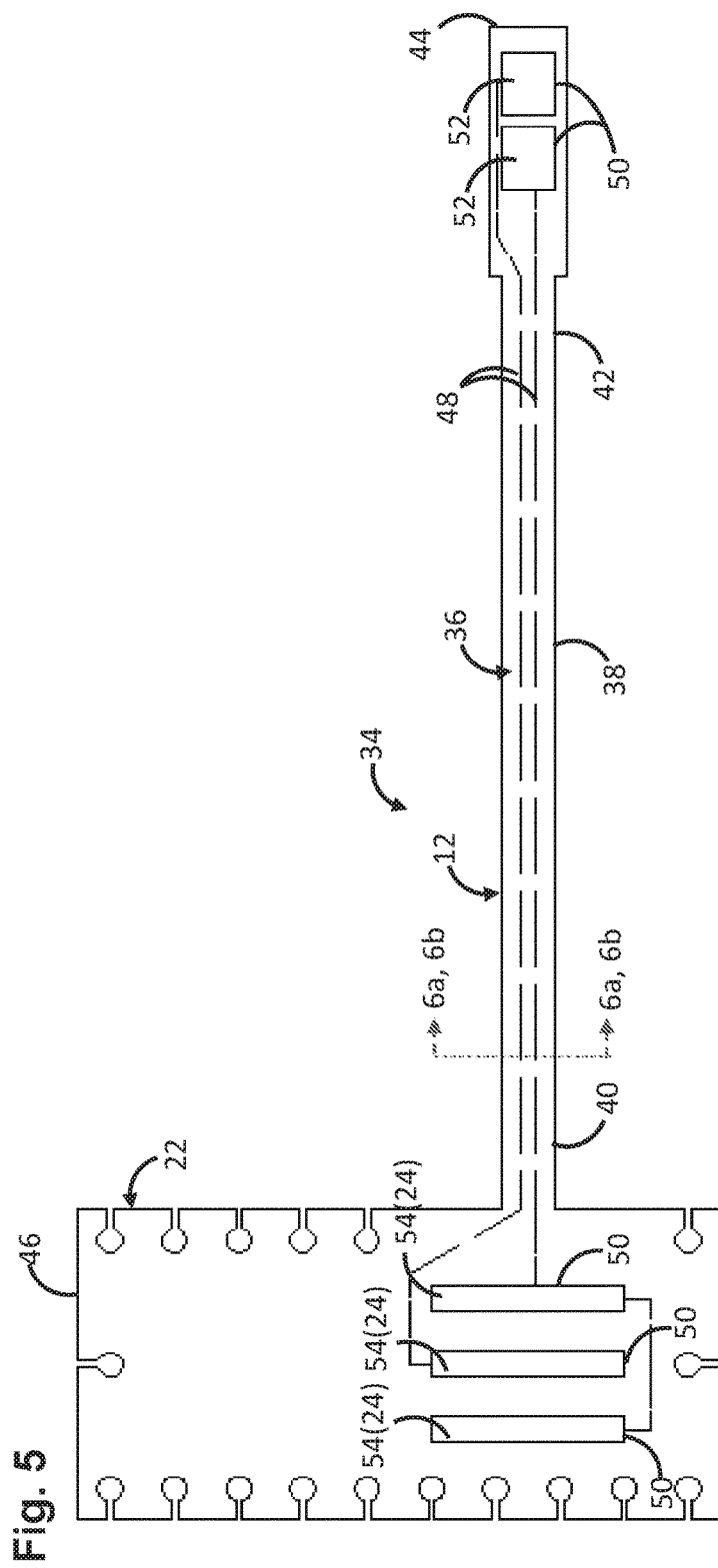
FIG. 5 is a plan view of the flexible circuit of FIG. 4.

In the illustrated embodiment, the electrode lead 10 is formed, at least partially, from an easily manufacturable flexible circuit 34, as best illustrated in FIGS. 4 and 5. To this end, the flexible circuit 34 comprises a planar dielectric substrate 36, which in the illustrated embodiment, is composed of liquid crystal polymer (LCP). LCP is inert in biological environments and is substantially impermeable to moisture, oxygen, and other gases and liquids. LCP is low cost and light weight, and can be precision molded and sealed using conventional thermoplastic welding techniques to create a substantially impermeable seal. Polyimide may alternatively be used for the planar dielectric substrate 12. However, LCP has one-tenth of the moisture uptake, and advantageously is compatible with both semiconductor processes and layer-to-layer lamination by fusion bonding of multiple LCP sheets with heat and pressure without the use of adhesives.

The planar dielectric substrate 36 generally includes an elongated lead substrate portion 38 that forms the lead body 12 of the electrode lead 10. The lead substrate portion 38 has one end 40 corresponding to the proximal end 14 of the lead body 12, and an opposing end 42 corresponding to the distal end 16 of the lead body 12. The planar dielectric substrate 36 further includes a connector substrate portion 44 disposed at the one end 40 of the lead substrate portion 38, and an enlarged cuff substrate portion 46 disposed at the other end 42 of the lead substrate portion 38. The connector substrate portion 44 forms at least a portion of the connector 18 of the electrode lead 10 (shown in FIG. 1), and the cuff substrate portion 46 forms the cuff body 22 of the electrode lead 10 (shown in FIG. 1). In the illustrated embodiment, the connector substrate portion 44 and cuff substrate portion 46 are rectangular in nature.

The flexible circuit 34 further comprises electrically conductive traces 48 embedded within the planar dielectric substrate 36, and extend from the connector substrate portion 44 to the enlarged cuff substrate portion 46. The electrically conductive traces 48 may be composed of a suitable electrically conductive and biocompatible material, such as gold, or 90/10 or 80/20 Platinum-Iridium alloy.

The flexible circuit 34 further comprises windows 50 formed in the planar dielectric substrate 36, and in particular, in the connector substrate portion 44 and the cuff substrate portion 46, that respectively exposes portions of the electrically conductive traces 48 to form connector pads 52 and electrode pads 54. As will be described in further detail below, the connector pads 52 may be used as the lead connector contacts 20 themselves or may be used to connect the electrically conductive traces 48 to the lead connector contacts 20. In the illustrated embodiments described herein, the electrode pads 54 are used as the electrode contacts 24 themselves, although in alternative embodiments, the electrode contacts 24 may be separate and distinct from the electrode pads 54 and may, thus, be coupled to the electrode pads 54. The unexposed portions of the electrically conductive traces 48 form the electrical conductors 26 of the electrode lead 10 (shown in FIG. 1).

Figure 6B:
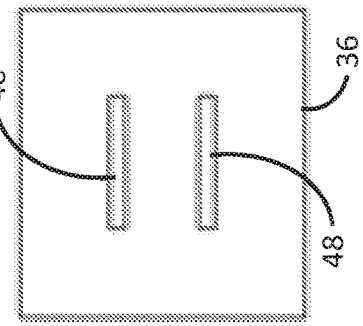
FIG. 6b is a cross-sectional view of the flexible circuit showing one embodiment of an arrangement of electrically conductive traces, taken along the line 6b-6b.
Figure 6A:
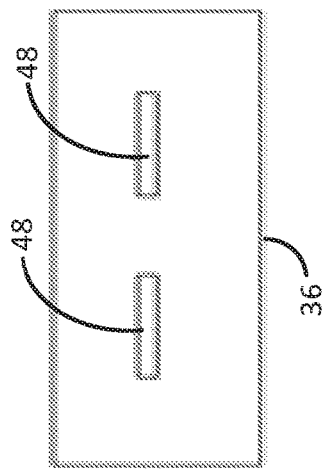

The electrically conductive traces 48 may be disposed in the planar dielectric substrate 36 side-by-side in a single layer, as illustrated in FIG. 6a, or as stacked multiple layers, as illustrated in FIG. 6b. As illustrated in FIGS. 4 and 5, the portions of the electrically conductive traces 48 that form the connector pads 52 and electrode pads 54 are many times larger in terms of surface area than the portions of the electrically conductive traces 48 that form the electrical conductors 26.

In one embodiment illustrated in FIGS. 7a and 8a, each connector pad 52 or electrode pad 54 is not interlocked in place by the edges 56 of the respective window 50, such that no portion of the connector pad 52 or electrode pad 54 is embedded in the planar dielectric substrate 36. In this case, the size and geometry of the window 50 will be the same size and geometry as the respective connector pad 52 or electrode pad 54.

In another embodiment illustrated in FIGS. 7b and 8b, each connector pad 52 or electrode pad 54 is interlocked in place by the edges 56 of the respective window 50, such that only the peripheral region 58 of the connector pad 52 or electrode pad 54 is embedded in the planar dielectric substrate 36. In this case, the size of the window 50 will be smaller than the size of the respective connector pad 52 or electrode pad 54. It can be appreciated that because the overlapping edges 56 of the window 50 lock the respective connector pad 52 or electrode pad 54 in place, delamination of the respective terminal 20 or electrode pad 54 from the planar dielectric substrate 26, that may otherwise be initiated at the edges 60 of the connector pad 52 or electrode pad 54, is prevented or at least minimized.

In still another embodiment illustrated in FIGS. 7c and 8c, each connector pad 52 or electrode pad 54 is interlocked in place by the edges 56 of the multiple respective windows 50 (in this case, two windows), such that a peripheral region 58 and additional interior regions 62 (in this case, one portion) of the connector pad 52 or electrode pad 54 are embedded in the planar dielectric substrate 36. In this case, the sizes of the windows 50 will be less than half the size of the respective connector pad 52 or electrode pad 54. The interior regions 62 that are embedded in the planar dielectric substrate 36 are smaller than the size of the windows 50, such that the respective connector pad 52 or electrode pad 54 electrically functions as a single connector pad 52 or electrode pad 54. It can be appreciated that because planar dielectric substrate 36 locks the respective connector pad 52 or electrode pad 54 at the interior regions 62 in addition to the peripheral region 58, delamination of the respective terminal 20 or electrode pad 54 from the planar dielectric substrate 26, that may otherwise be initiated at the edges 60 or interior region 62 of the connector pad 52 or electrode 24, is further prevented or minimized.

Figure 9:
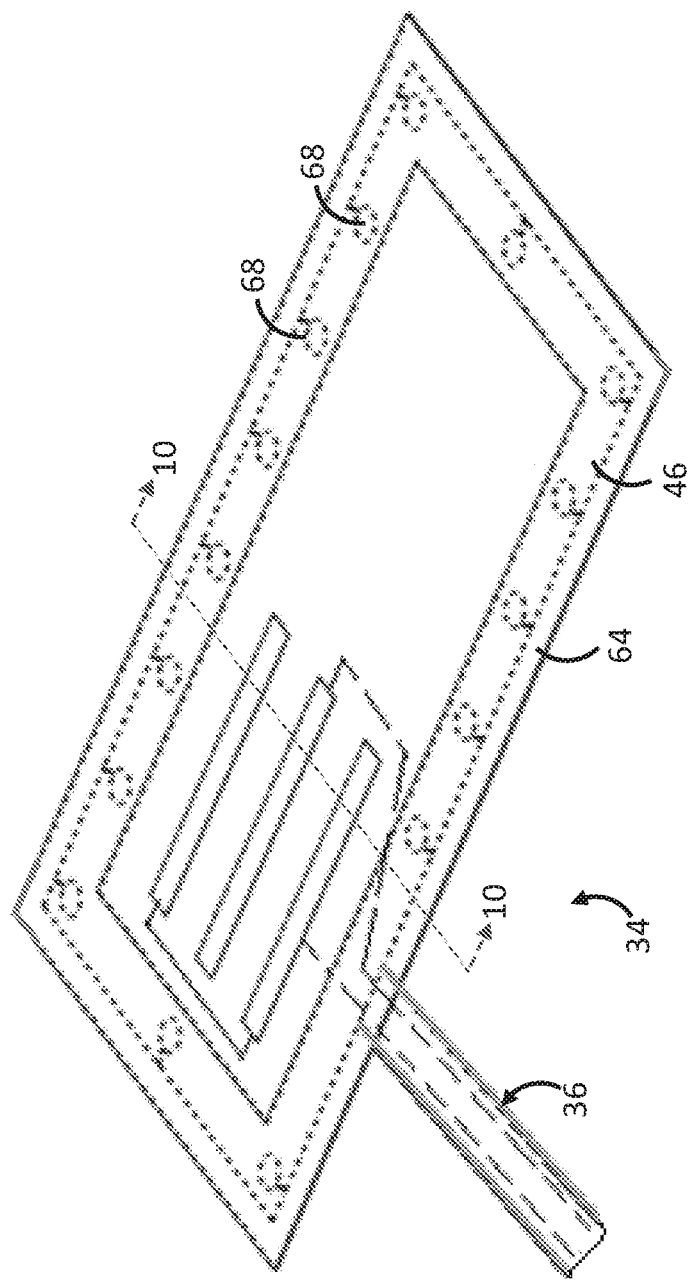
FIG. 9 is a perspective view of one embodiment of a cuff substrate portion that includes the flexible circuit of FIG. 5, particularly showing an elastic layer disposed over the cuff substrate portion.
Figure 10:
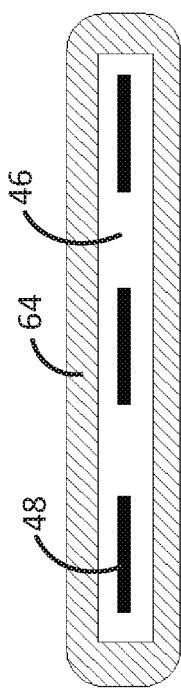
FIG. 10 is a cross-sectional view of the cuff substrate portion of FIG. 9, taken along the line 10-10.

As best illustrated in FIGS. 9 and 10, the flexible circuit 34 may further comprise one or more layers of an elastic, electrically insulative, biocompatible, material 64, such as, e.g., silicone, polyurethane, polyether polyurethane, polycarbonate polyurethane, parylene, perfluoroalkoxy alkanes (PFA), and polytetrafluoroethylene (PTFE), disposed over the cuff substrate portion 46 of the planar dielectric substrate 36. The elastic layer 64 allows implantation of the completed electrode lead 10 within a patient without cutting surrounding tissue, which may otherwise occur due to the sharp edges of the planar dielectric substrate 36. As illustrated in FIG. 11, the flexible circuit 34 may optionally comprise an anti-inflammatory coating 66 (represented by the hashed lines) disposed over or as part of the cuff substrate portion 46. The anti-inflammatory coating 66 releases an anti-inflammatory drug, such as a steroid dexamethasone, into surrounding tissue over time, thereby providing therapeutic effects following implantation of the electrode lead 10 by reducing subsequent nerve inflammation and swelling. Notably, the windows 50 described above will not only be formed through the planar dielectric substrate 36, but will be formed through the elastic layer 64 and optional anti-inflammatory coating 66, to form the connector pads 52 and electrode pads 54.

Figure 12C:
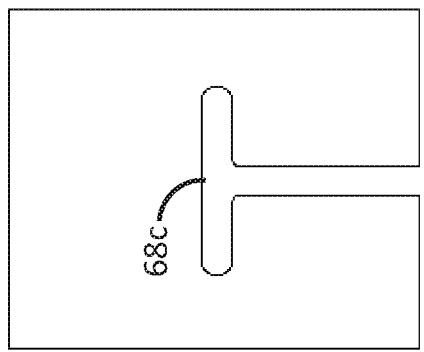
FIG. 12c is still another embodiment of an open slot formed in the cuff substrate portion of FIG. 9.
Figure 12B:
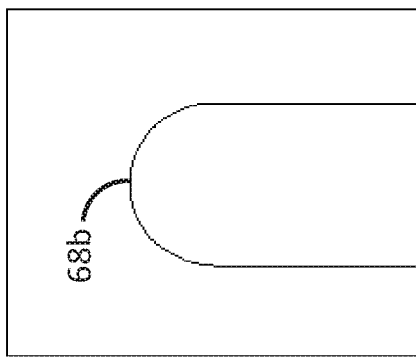
FIG. 12b is another embodiment of an open slot formed in the cuff substrate portion of FIG. 9.
Figure 12A:
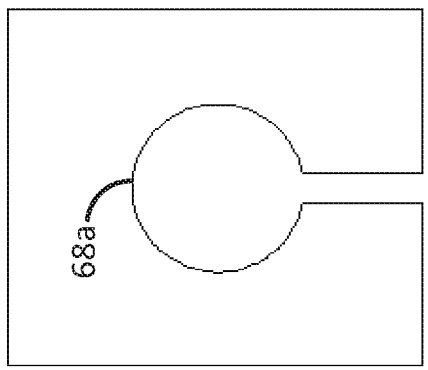
FIG. 12a is one embodiment of an open slot formed in the cuff substrate portion of FIG. 9.

The electrode lead 10 may further comprise a plurality of open slots 68 disposed along the periphery of the cuff body 22 to facilitate the anchoring of the elastic layer 64 to the cuff substrate portion 46 of the planar dielectric substrate 36. That is, the elastic layers 64 on both sides of the cuff substrate portion 46 interlocks with each other through the open slots 68. Furthermore, the shape and size of the open slots 68 can be selected to influence the rigidity (i.e., the curling stiffness) of the cuff body 22. That is, as the number of open slots 68 or the size of the open slots increases, the rigidity of the cuff body 22 will decrease. As examples, the open slots 68 may take the form of slotted holes 68a (FIG. 12a), rounded slots 68b (FIG. 12b), or a slotted "Ts" 68c (FIG. 12c).

Figure 13A:
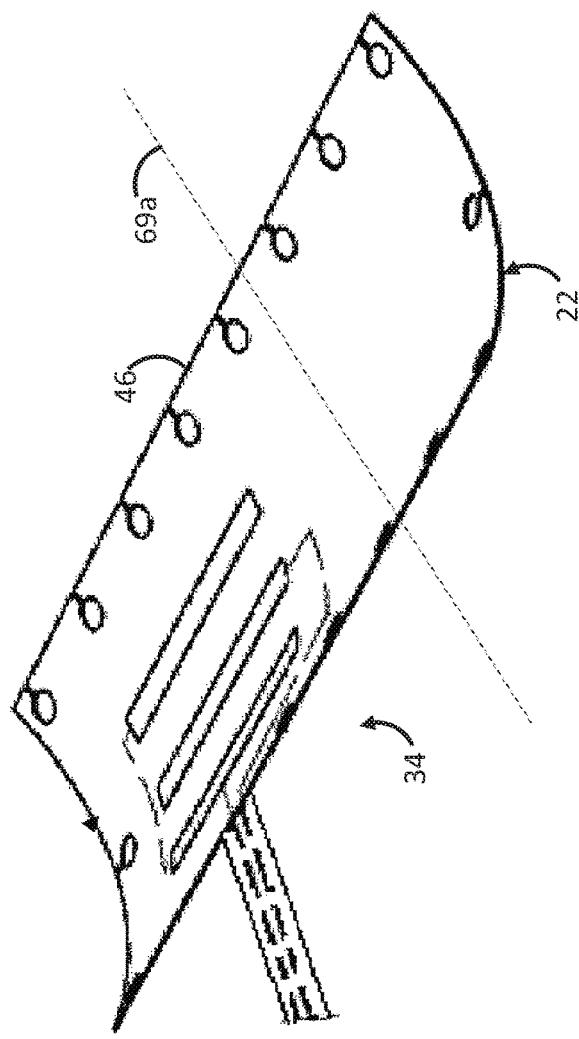
FIG. 13a is a perspective view of the cuff substrate portion of the FIG. 9 in an unfurled stable configuration.
Figure 13B:
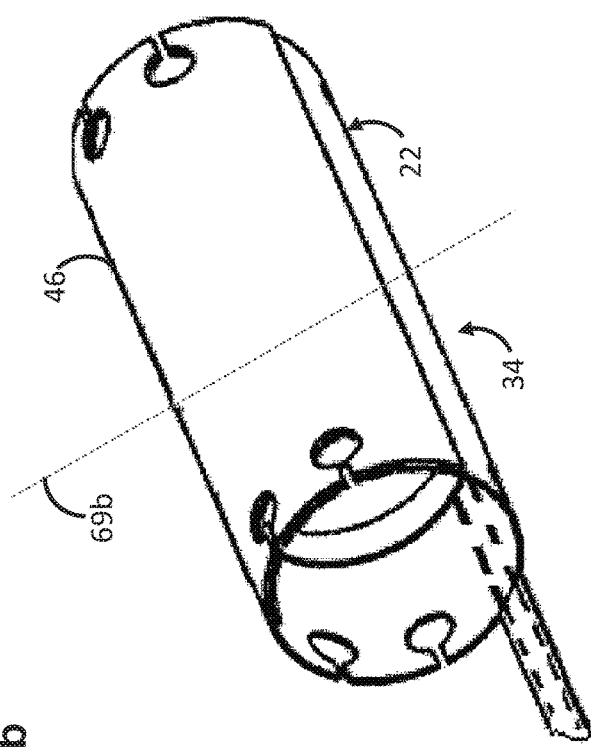
FIG. 13b is a perspective view of the cuff substrate portion of the FIG. 9 in a furled stable configuration.

Referring now to FIGS. 13a and 13b, the cuff body 22, and in the illustrated embodiment the cuff substrate portion 46 of the flexible circuit 34, may be pre-shaped to curve in two orthogonal directions (in this case, pre-shaped to curve along a lateral axis 69a in FIG. 13a, and pre-shaped to curve along a longitudinal axis 69b in FIG. 13b), such that the cuff body 22 has a bi-stable structure. For example, the cuff body 22 may be configured between in an unfurled stable configuration (FIG. 13a), which facilitates handling and placement of the cuff body 22 underneath the nerve 28, and a furled stable configuration (FIG. 13b), which facilitates placement of the cuff body 22 around the nerve 28. When the cuff body 22 is in the unfurled state, in the absence of external force, the lateral curve provides an additional bending stiffness in the cuff body 22 that overcomes the bending force imposed on the cuff body 22 by the longitudinal curve, such that the cuff body 22 is maintained in the unfurled state. However, when a torqueing force is applied to the cuff body 22 along the longitudinal axis 69b, the additional ending stiffness in the cuff body 22 provided by the lateral curve can be overcome, such that the cuff body 22 is placed into the furled stable state by the bending force imposed on the cuff body 22 by the longitudinal curve.

Figure 14:
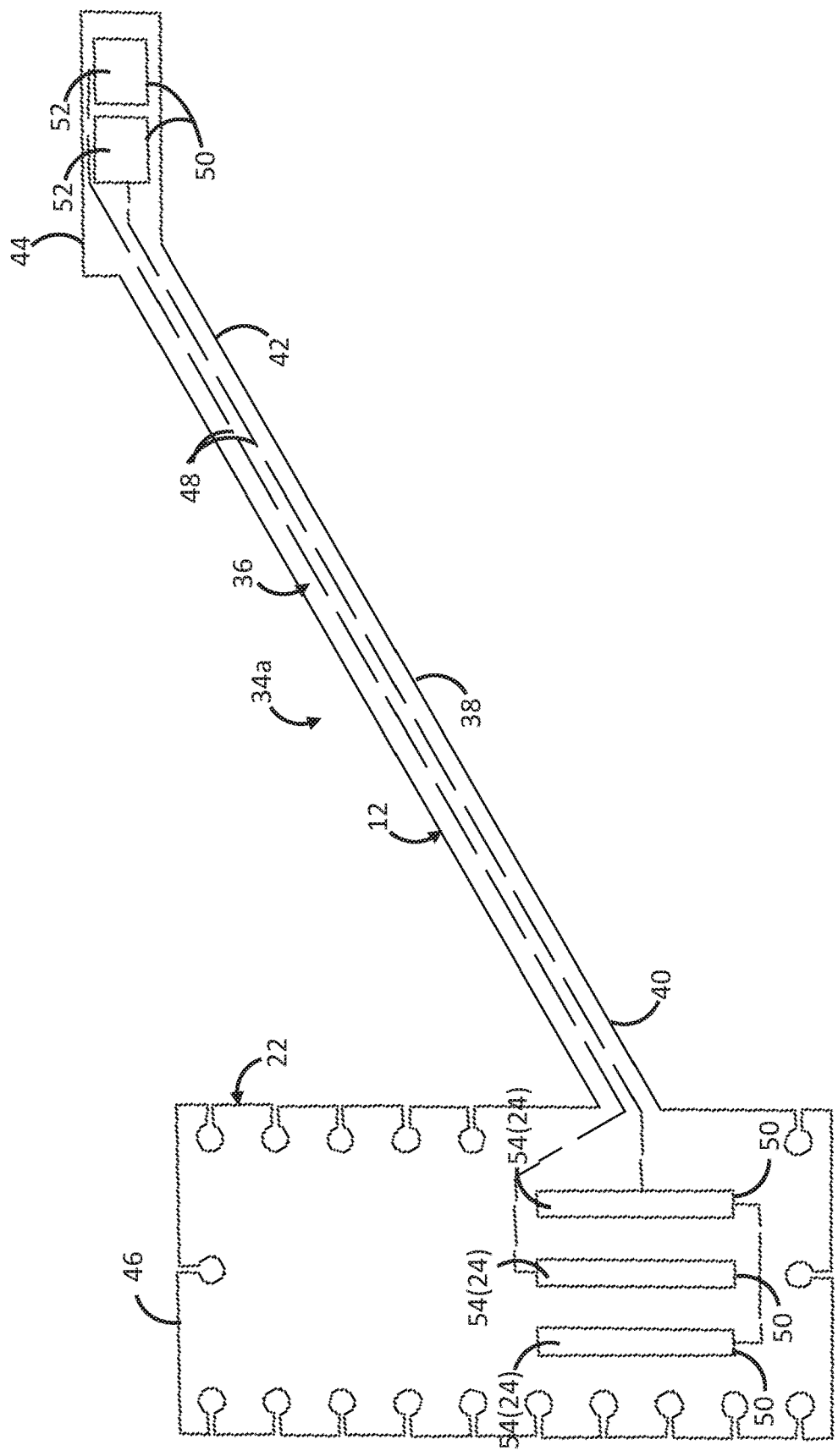
FIG. 14 is a plan view of another embodiment of a flexible circuit that can be used to manufacture the electrode lead of FIG. 1.

Although the connector substrate portion 44 and the cuff substrate portion 46 are illustrated in FIGS. 4 and 5 as being oriented perpendicularly to the lead substrate portion 38, an alternative embodiment of a flexible circuit 34a may be identical to the flexible circuit 34 described in FIGS. 4 and 5, with the exception that the connector substrate portion 44 and the cuff substrate portion 46 may be oriented obliquely to the lead substrate portion 38, as illustrated in FIG. 14. This arrangement facilitates the coiling of the lead body 12 into an actual coil configuration, so that the cuff body 22 can be positioned perpendicularly to the lead body 12. If the cuff substrate portion 46 is oriented perpendicularly to the connector substrate portion 44 before it is coiled, the final position of the cuff body 22 will be skewed and will not be perpendicular to the coiled lead body 12.

Figure 15:
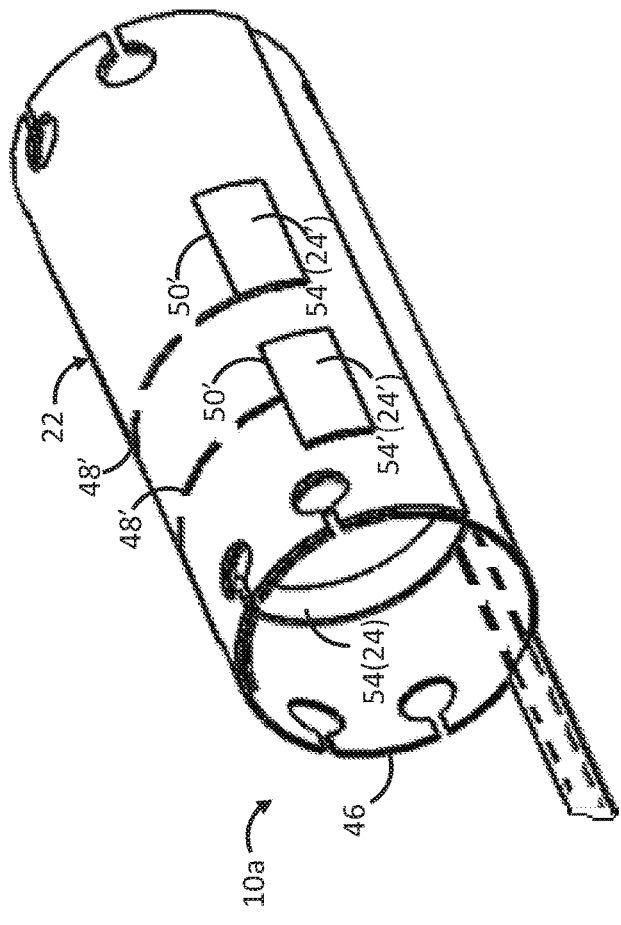
FIG. 15 is a perspective view of a flexible circuit that may be part of a cuff body of an electrode lead constructed in accordance with another embodiment of the present invention.

In the embodiment of the electrode lead 10 illustrated in FIG. 1, only electrode contacts 24 that serve as stimulation electrodes are described. An alternative embodiment of an electrode lead 10a may be identical to the electrode lead 10 illustrated in FIG. 1, with the exception that recording electrode contacts 24' are located on the outer surface of the cuff body 22 when circumferentially disposed around a nerve (not shown), as illustrated in FIG. 15. In this case, additional connector contacts (not shown) may be located on the lead connector (not shown) for electrically coupling to the additional electrode contacts 24'. Notably, the cuff body 22 of the electrode lead 10a may be circumferentially disposed around a nerve, and therefore, the recording electrode contacts 24' may be used to sense EMG signals in muscle surrounding the nerve, while the stimulation electrode contacts 24 are used to stimulate the nerve.

Figure 16:
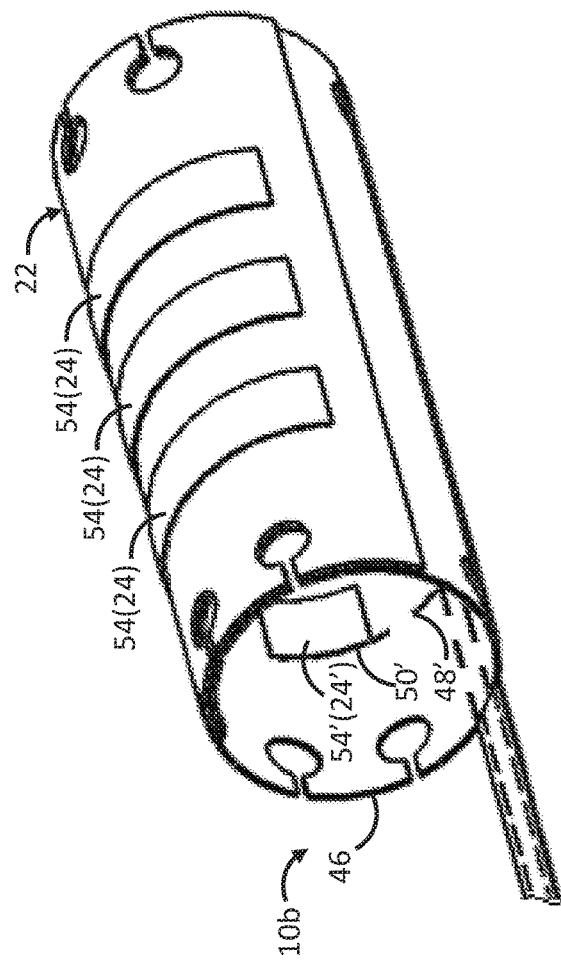
FIG. 16 is a perspective view of a flexible circuit that may be part of a cuff body of an electrode lead constructed in accordance with still another embodiment of the present invention.

In another alternative embodiment of an electrode lead 10b, as illustrated in FIG. 15, the stimulation electrode contacts 24 can be located on the outer surface of the cuff body 22, and the recording electrode contacts 24' can be located on the inner surface of the cuff body 22. In the same manner that the stimulating electrode contacts 24 are provided in the flexible circuit 34 illustrated in FIGS. 4 and 5, the recording electrode contacts 24' illustrated in FIGS. 15 and 16 can be provided by forming windows 50' in the planar dielectric substrate 26, and in particular the cuff substrate portion 46, to expose portions of electrically conductive traces 48' to form electrode pads 54' corresponding to the recording electrode contacts 24'.

Figure 17:
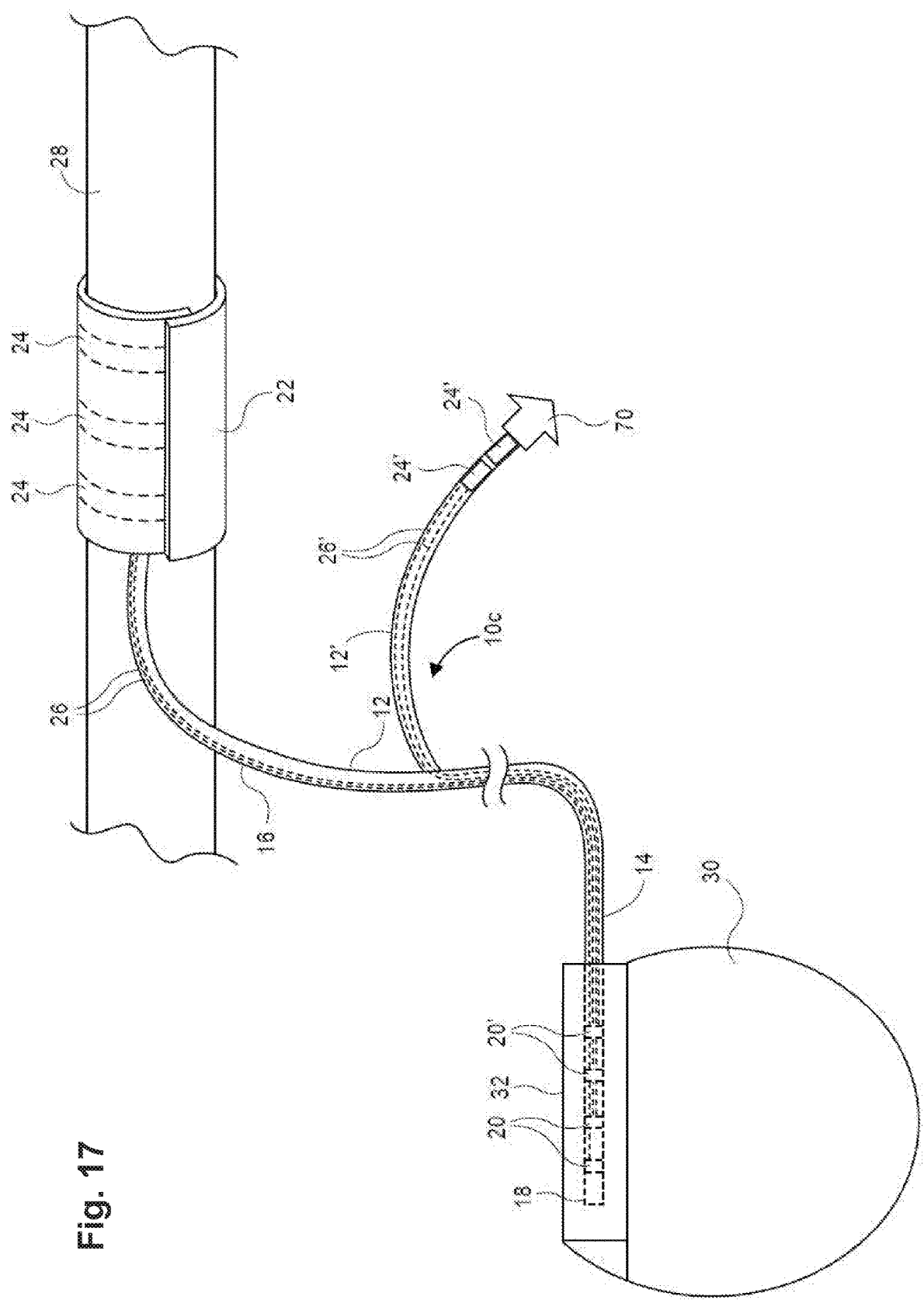
FIG. 17 is a perspective view of an electrode lead constructed in accordance with yet another embodiment of the present invention, wherein a cuff body of the electrode lead is particularly shown disposed on a nerve.

Referring to FIG. 17, an alternative embodiment of an electrode lead 10c is similar to the electrode lead 10 illustrated in FIG. 1, with the exception that the electrode lead 10c comprises a branch lead body 12' extending from the lead body 12 (as the main lead body 12), at least one additional connector contact 20' (two shown) disposed on the lead connector 18, at least one additional electrode contact 24' (two shown) disposed on the branch lead body 12', and at least one electrical conductor 26' (two shown) extending through the main lead body 12 and branch lead body 12' between the additional lead connector contacts 20' and the additional electrode contacts 24'.

The electrode lead 10c further comprises a barb 70 formed at the end of the branch lead body 12', which can be used to anchor the branch lead body 12' and the corresponding electrode contacts 24' to muscle remotely located from the nerve 28. Notably, anchoring of the branch lead body 12' to the muscle will occur as tissue grows and envelopes around the barb 70, and thus, the barb 70 need not be rigid. The electrode contacts 24' may be used as sensors to detect physiological signals, such as EMG signals, in the muscle in which the branch lead body 12' is anchored via the barb 70.

Figure 18:
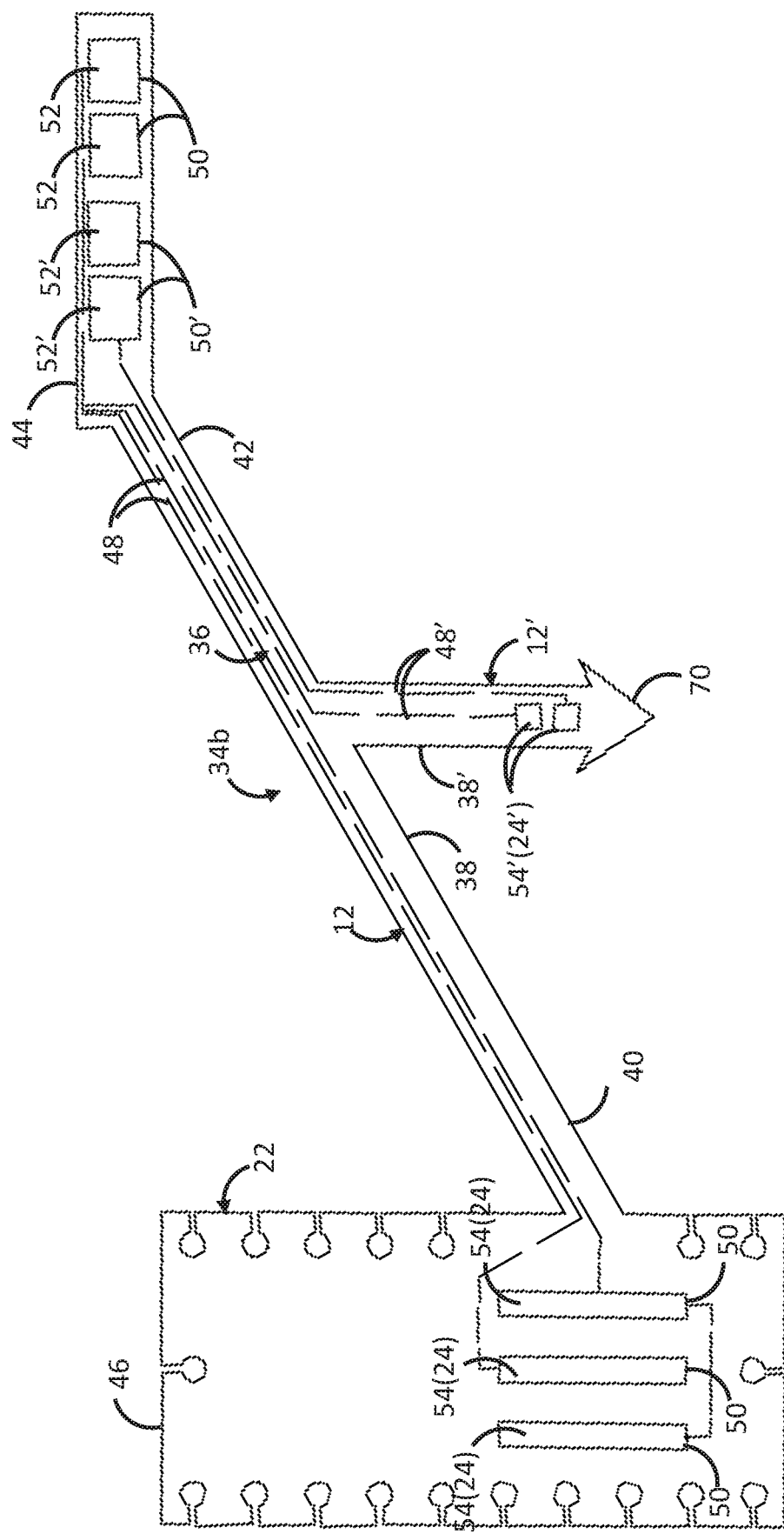
FIG. 18 is a plan view of one embodiment of a flexible circuit that forms a portion of the electrode lead of FIG. 17.

In this embodiment, the electrode lead 10c will be formed, at least partially, from a flexible circuit 34b that is similar to the flexible circuit 34, with the exception that the planar dielectric substrate 26 includes an additional elongated branch lead substrate portion 38' extending from the lead substrate portion 38 (as the main lead substrate portion), as illustrated in FIG. 18. The flexible circuit 34b comprises additional electrically conductive traces 48' embedded within the planar dielectric substrate 36 and extending from the connector substrate portion 44 to the branch lead substrate portion 68. The flexible circuit 34b further comprises windows 50' formed through the planar dielectric substrate 36, and in particular, in the connector substrate portion 44 and the branch lead substrate portion 12', that respectively exposes portions of the electrically conductive traces 48' to form the two additional connector pads 52' and the two additional electrode pads 54'.

As will be described in further detail below, the connector pads 52' may be used as the lead connector contacts 20' themselves or may be used to connect the electrically conductive traces 48' to the lead connector contacts 20'. In the illustrated embodiments described herein, the electrode pads 54' are used as the electrode contacts 24' themselves, although in alternative embodiments, the electrode contacts 24' are distinct from the electrode pads 54' and may be coupled to the electrode pads 54'. The unexposed portions of the electrically conductive traces 48' form the electrical conductors 26'. The distal end of the branch lead substrate portion 68 will be shaped into the form of the barb 70.

Figure 19:
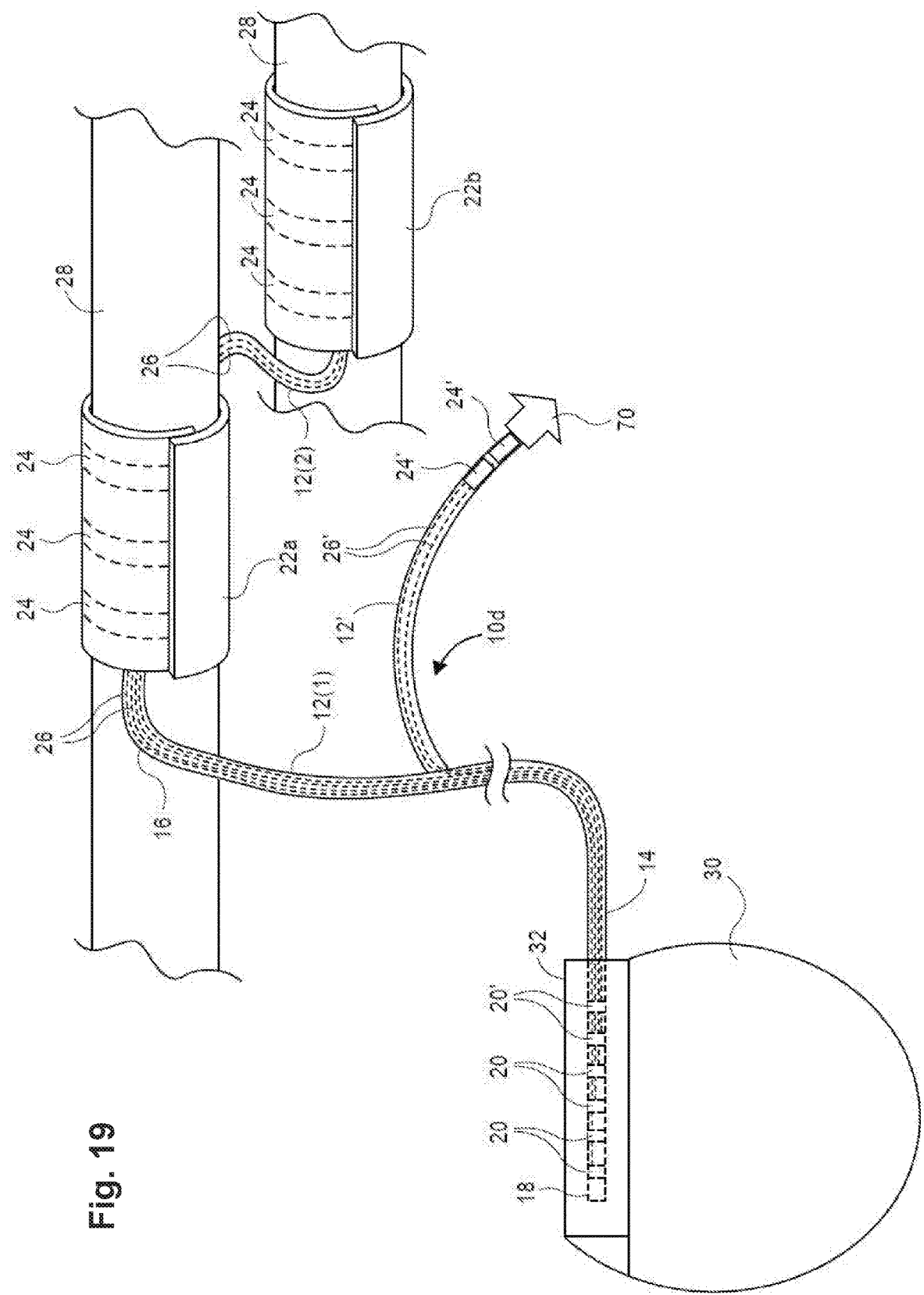
FIG. 19 is a perspective view of an electrode lead constructed in accordance with yet another embodiment of the present invention, wherein two cuff bodies of the electrode lead are particularly shown disposed on two nerves.

Referring to FIG. 19, an alternative embodiment of an electrode lead 10d is similar to the electrode lead 10c illustrated in FIG. 17, with the exception that the electrode lead 10d comprises a proximal cuff body 22a in addition to a distal cuff body 22b, at least one additional connector contact 20 (four total connector contacts 20 shown) disposed on the lead connector 18, at least one additional electrode contact 24 (four electrode contacts 24 shown) disposed on the proximal cuff body 22a and distal cuff body 22b, and at least one electrical conductor 26 (four total electrical conductors 26 shown) extending through the main lead body 12 between the lead connector contacts 20 and the electrode contacts 24. The proximal cuff body 22a is located along the lead body 12 between the lead connector 18 and the distal cuff body 22b.

The lead body 12 may be divided into a proximal lead body portion 12(1) extending between the lead connector 18 and the proximal cuff body 22a, and a distal lead body portion 12(2) extending between the proximal cuff body 22a and the distal cuff body 22b. The lengths of the lead body portions 12(1), 12(2) may be configured for allowing the cuff bodies 22a, 22b to be placed around bilateral sections of the same nerve, such as, e.g., the hypoglossal nerve in the neck, and the branch lead body 12' may be anchored into muscle, such that the electrode contacts 24' can detect the patency of the upper airway. Specifically, the electrode contacts 24' may be positioned, such that it can detect EMG signals on the genioglossus muscle or other upper airway muscles.

In the illustrated embodiment, the branch lead body 12' is located between the lead connector 18 and the proximal cuff body 22a, although in alternative embodiments, the branch lead body 12' may be located between the proximal cuff body 22a and the distal cuff body 22b. In still another embodiment, the electrode lead 10c may not have the branch lead body 12'. Although the electrode lead 10c is illustrated with only two cuff bodies 22a, 22b, the electrode lead 10c may alternatively include more than two cuff bodies. In alternative embodiments, the lead body 12 may be split into plurality distal ends on which cuff bodies 22 may be disposed.

Figure 20:
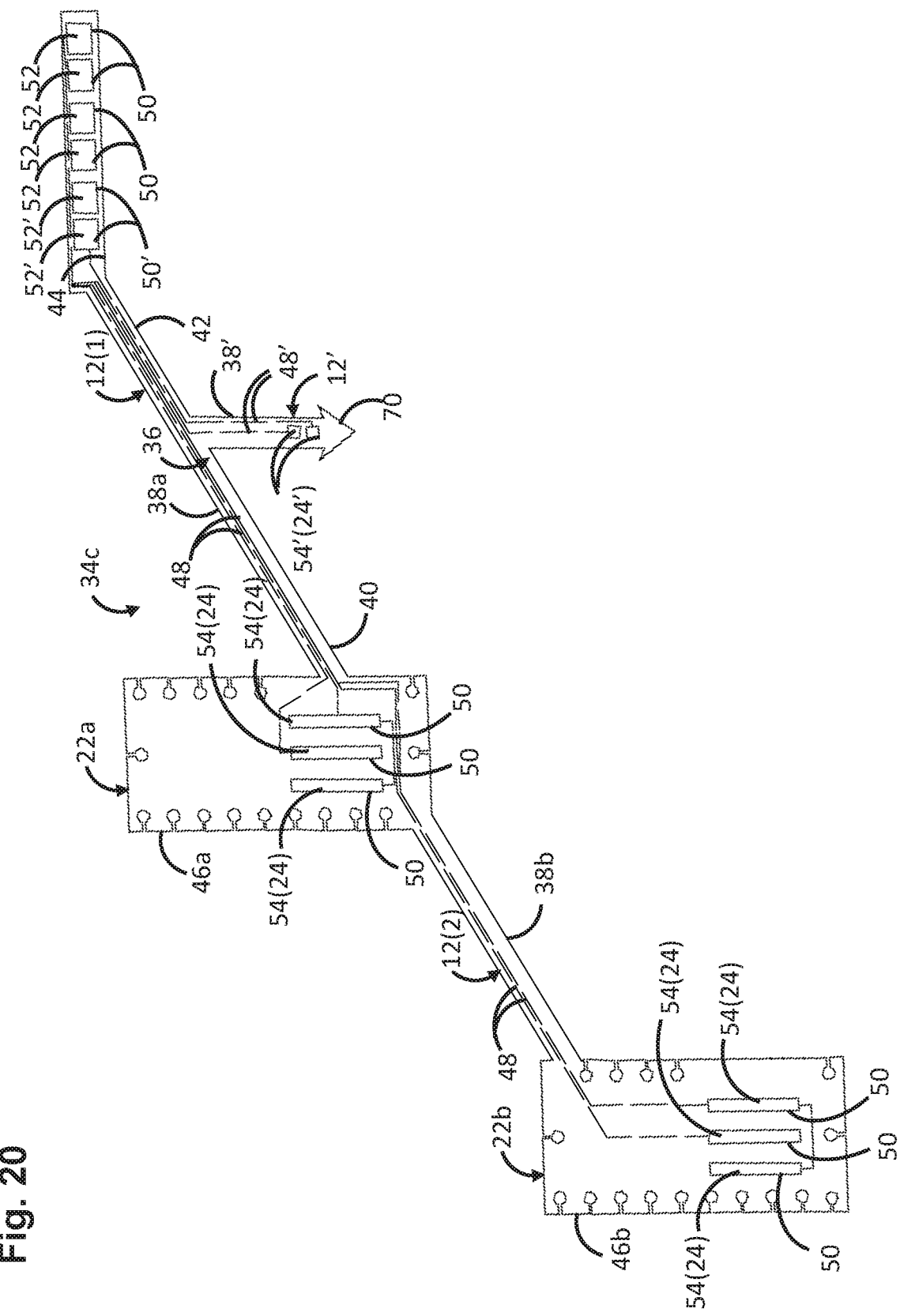
FIG. 20 is a plan view of one embodiment of a flexible circuit that forms a portion of the electrode lead of FIG. 19.

In this embodiment, the lead body 12c will be formed, at least partially, from a flexible circuit 34c that is similar to the flexible circuit 34b, with the exception that the planar dielectric substrate 26 includes a first enlarged cuff substrate portion 46a in addition to the second cuff substrate portion 46b, as illustrated in FIG. 20. The first cuff substrate portion 46a is located along the lead substrate portion 38 between the second cuff substrate portion 46b and the branch lead substrate portion 38'. Thus, the lead substrate portion 38 can be divided into a first elongated lead substrate portion 38a that extends between the connector substrate portion 44 and the first cuff substrate portion 46', and a second elongated lead substrate portion 38b that extends between the first cuff substrate portion 46' and the second cuff substrate portion 46. In the alternative embodiment where the branch lead body 12' is located between the first cuff body 22a and the second cuff body 22b, the branch lead substrate portion 38' may likewise be located between the first cuff substrate portion 46a and the second cuff substrate portion 46b.

The flexible circuit 34c comprises electrically conductive traces 48 embedded within the planar dielectric substrate 36 and extending from the connector substrate portion 44 to the first and second cuff substrate portions 46a, 46b. The flexible circuit 34c further comprises windows 50 formed through the planar dielectric substrate 36, and in particular, in the connector substrate portion 44 and the first and second cuff substrate portions 46a, 46b, that respectively expose portions of the electrically conductive traces 48 to form four connector pads 52 and four additional electrode pads 54.

As will be described in further detail below, the connector pads 52 may be used as the lead connector contacts 20 themselves or may be used to connect the electrically conductive traces 48 to the lead connector contacts 20. In the illustrated embodiments described herein, the electrode pads 54 are used as the electrode contacts 24 themselves, although in alternative embodiments, the electrode contacts 24 are distinct from the electrode pads 54 and may be coupled to the electrode pads 54. The unexposed portions of the electrically conductive traces 48 form the electrical conductors 26.

The lead bodies 12 in the electrodes leads 10 described above may be variously configured, depending on the flexibility requirements of the particular application of the electrode lead 10. If minimal lateral flexibility is required, a lead body 12a, which is planar by virtue of the lead substrate portion 38 of the planar dielectric substrate 36 from which it is composed, may remain flat and straight, as illustrated in FIG. 21a. Notably, LCP is relatively inflexible, and thus, the lead 12a illustrated in FIG. 20a will not flex along the plane of the lead 12a.

If additional lateral flexibility is required, the lead substrate portion 38 of the planar dielectric substrate 36 can be pre-shaped into a three-dimensional structure that increases the flexibility of the lead substrate portion 38 in the plane of the dielectric substrate 36. As one example, the three-dimensional structure may be a helical structure that forms a lead body 12b, as illustrated in FIG. 21b. Thus, the helical structure provides the lead body 12b with a wider range of movement in all three dimensions relative to the lead body 12a. The lead body 12b may further comprise an outer layer of insulative material 72 disposed over the helical structure, as illustrated in FIG. 21c. The insulative material 72 may be composed of one of silicone, polyurethane, polyether polyurethane, polycarbonate polyurethane, parylene, perfluoroalkoxy alkanes (PFA), and polytetrafluoroethylene (PTFE). In the illustrated embodiment, the insulative material 72 takes the form of tubing composed of a soft polymer, such as, e.g., silicone, over the helical structure. The soft polymer tubing 72 may prevent the sharp edges of the lead substrate portion 38 of the planar dielectric substrate 26 from injuring the living tissue adjacent the electrode lead 10.

Figure 21D:
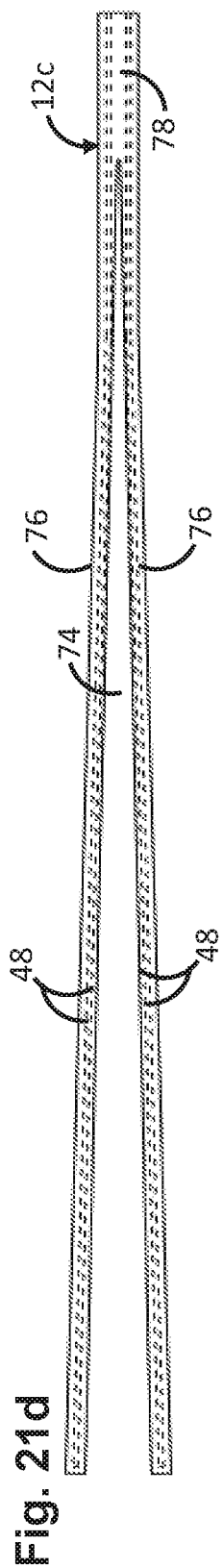
FIG. 21d is a plan view of still another embodiment of a lead body of the electrode lead of FIG. 1.
Figure 21E:
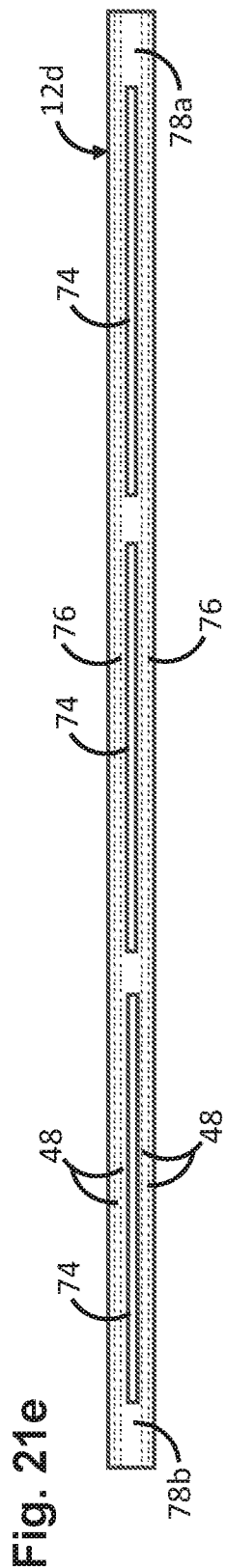
FIG. 21e is a plan view of yet another embodiment of a lead body of the electrode lead of FIG. 1.

Alternatively, if additional lateral flexibility is required, the lead substrate portion 38 of the planar dielectric substrate 36 may have at least one slit 74 (only one shown) formed between the electrically conductive traces 48, thereby forming a lead body 12c having a plurality of planar strands 76 (only two shown), as illustrated in FIG. 21d. As there shown, the slit 74 extends through the one end of the lead substrate portion 38 (and in this case, the distal end of the lead body 12c), such that an end portion 78 of the lead substrate portion 38 remain intact, and the planar strands 76 have loose ends. In this case, multiple cuff bodies 22 (not shown) can be respectively disposed on the loose ends of the planar strands 76. Alternatively, the slits 74 may not extend through either end of the lead substrate portion 38, such that both end portions 78a, 78b of the lead substrate portion 38 remains intact, thereby forming a lead body 12d, as illustrated in FIG. 21e. The slits 74 may be collinear in nature, such that the lead substrate portion 38 remains intact between the collinear slits 74. Thus, the slits 74 intermittently extend along the length of the lead substrate portion 38, such that planar strands 76 periodically split from each other and then join back to together at points along the length of the lead substrate portion 38.

Figure 21F:
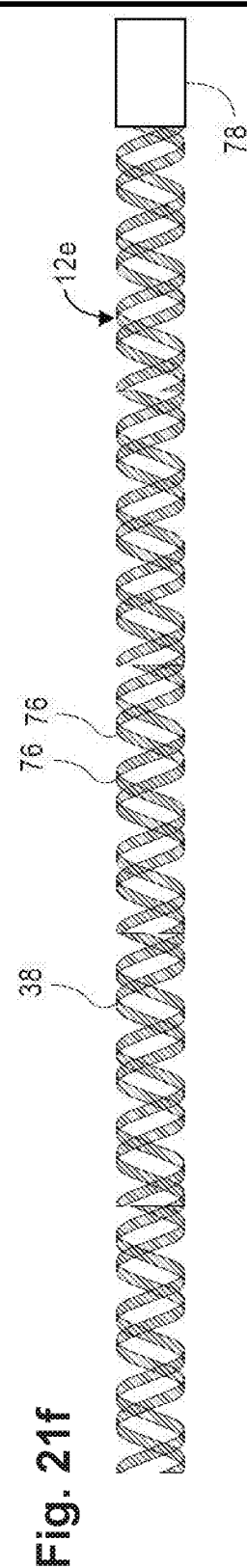
FIG. 21f is a plan view of yet another embodiment of a lead body of the electrode lead of FIG. 1.
Figure 21G:
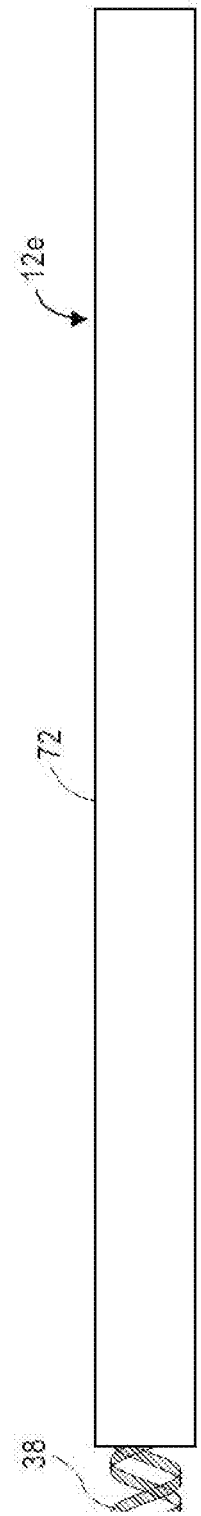
FIG. 21g is a plan view of the lead body of FIG. 21f with an additional insulating tube.

Because the widths of the planar strands 76 in the lead bodies 12c, 12d of FIGS. 21d and 21e are smaller than the lead substrate portion 38 and that the planar strands 76 can move relative to each other, the entireties of the lead bodies 12 are afforded a wider range of movement in all three dimensions relative to a single wider intact lead body 12a. In the case where the planar strands 76 of the lead body 12 have loose ends, as illustrated in FIG. 21d, the planar strands 76 may be pre-shaped into a co-helical structure (i.e., the helical structures are interleaved with each other) to form a lead body 12e, as illustrated in FIG. 21f. The lead body 12e may further comprise a tube 72 composed of a soft polymer, such as, e.g., silicone, over the co-helical structure, as illustrated in FIG. 21g.

Alternatively, if additional lateral flexibility is required, the lead substrate portion 38 of the planar dielectric substrate 36 may be pre-shaped into a sigmoid structure to form a lead body 12f, as illustrated in FIG. 21h. Like the helical structure described above, the sigmoid structure provides the lead body 12f with a wider range of movement. The lead body 12f may further comprise a tube 72 composed of a soft polymer, such as, e.g., silicone, over the sigmoid structure, as illustrated in FIG. 21i.

As briefly discussed above, the female connector 32 of the neurostimulation device 30 (shown in FIG. 1) is conventional in nature, and thus, it is desirable that the lead connector 18 be compatible with the connector 32 of the neurostimulation device 30. This requires that the lead connector 18 be cylindrical in nature, and that the connector contacts 20 be disposed around the circumference of the lead connector 18, such that when inserted into the connector 32 of the neurostimulation device 30 electrical connection between the electronics of the neurostimulation device 30 and the electrode contact 24 be created. However, because the connector substrate portions 44 of the flexible circuits 34 described herein are planar in nature, without significant modification, the flexible circuits 34 will not be compatible with conventional connectors 32.

Figure 22:
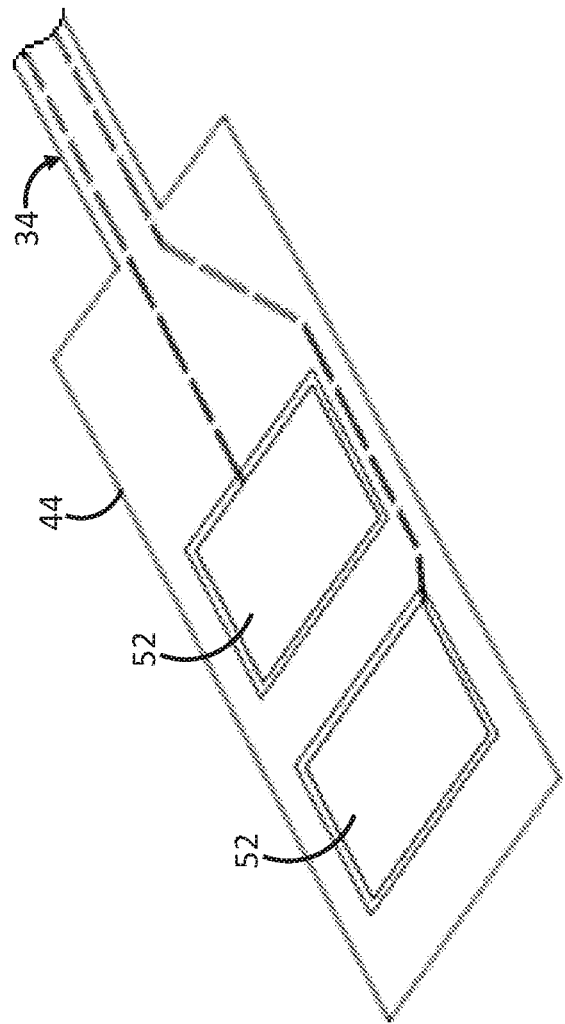
FIG. 22 is a perspective view of a connector substrate portion of the flexible circuit of FIG. 4.
Figure 23:
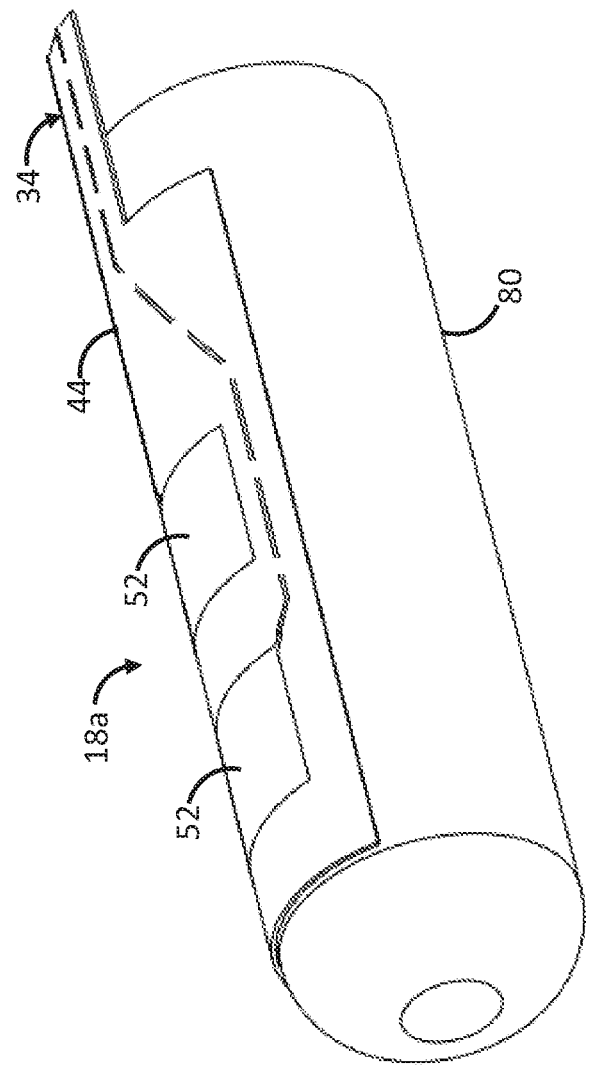
FIG. 23 is a perspective view of one embodiment of a lead connector of the electrode lead of FIG. 1 that can be formed from the connector substrate portion of FIG. 22.
Figure 25:
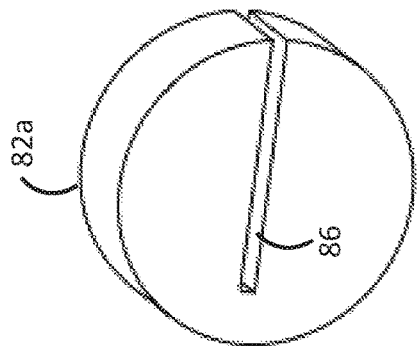
FIG. 25 is a perspective view of one embodiment of a rigid arcuate connector contact.

To this end, one embodiment of a lead connector 18a comprises the connector substrate portion 44 and connector pads 52 of the flexible circuit 34 described above, and a rigid cylindrical rod 80 having an outer surface on which the connector substrate portion 44 is affixed, as illustrated in FIGS. 22 and 23. The cylindrical rod 80 is sized to firmly fit within the female connector 32 of the neurostimulation device 30. The cylindrical rod 80 can be composed of any suitable material (e.g., stainless steel, polyurethane, or epoxy) that has the necessary column strength to allow the lead connector 18a to be inserted into the connector 32 of the neurostimulation device 30.

The connector substrate portion 44 may be thermoformed into the shape of the outer surface of the cylindrical rod 80 and affixed to the outer surface of the cylindrical rod 80 using suitable means, such as bonding, although in alternative embodiments, the connector substrate portion 44 may be affixed to the outer surface of the cylindrical rod 80 without thermoforming. The connector pads 52 of the flexible circuit 34 face outward away from the cylindrical rod 80 when the connector substrate portion 44 is affixed to the outer surface of the cylindrical rod 80. In this manner, the connector pads 52 will be exposed and will serve as the connector contacts 20 when the lead connector 18*a* is inserted into the connector 32 of the neurostimulation device 30.

Referring to FIGS. 24-27, another embodiment of a lead connector 18*b* comprises the connector substrate portion 44 and connector pads 52 of the flexible circuit 34 described above, at least one rigid arcuate connector contact 82*a* (two shown) affixed to the connector substrate portion 44 and electrically coupled respectively to the connector pads 52, and a generally cylindrical, rigid, electrical insulator 84 encapsulating the connector substrate portion 44 between and adjacent the connector contacts 82*a*, such that only the arcuate surfaces of the connector contacts 82*a* are exposed. In this manner, the connector contacts 82*a* will be exposed for electrical connection to the circuitry of the neurostimulation device 30 when the lead connector 18*a* is inserted into the connector 32 of the neurostimulation device 30. The electrical insulator 84 may be composed of a suitable material that can be over-molded over the connector substrate portion 44 and connector contacts 82*a*, such as, e.g., epoxy or polyurethane. The arcuate surfaces of the connector contacts 82*a* preferably conform with the outer surface of the electrical insulator 84, such that the lead connector 18*b* has a smooth continuous outer surface that facilitates its insertion into the connector 32 of the neurostimulation device 30.

Figure 27:
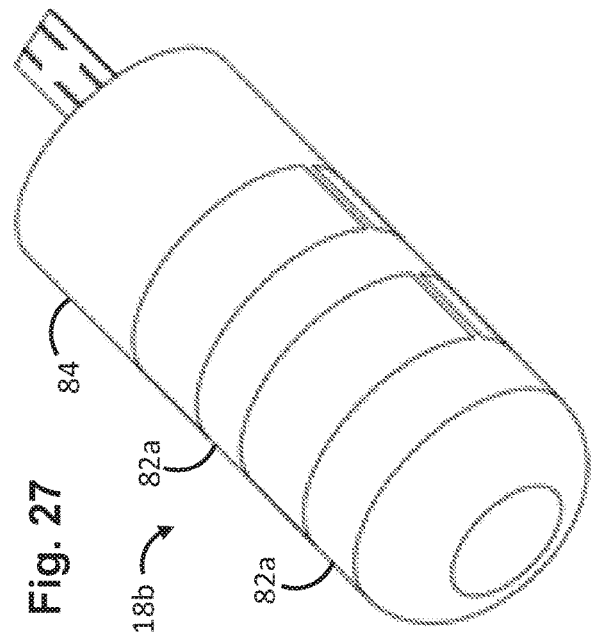
FIG. 27 is a perspective view of another embodiment of a lead connector of the electrode lead of FIG. 1 that can be formed from the assembly of FIG. 26.
Figure 24:
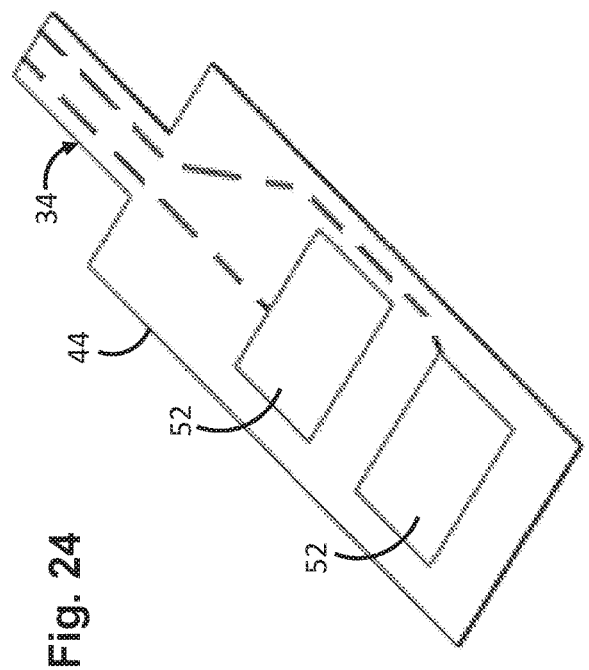
FIG. 24 is a perspective view of a connector substrate portion of the flexible circuit of FIG. 4.
Figure 26:
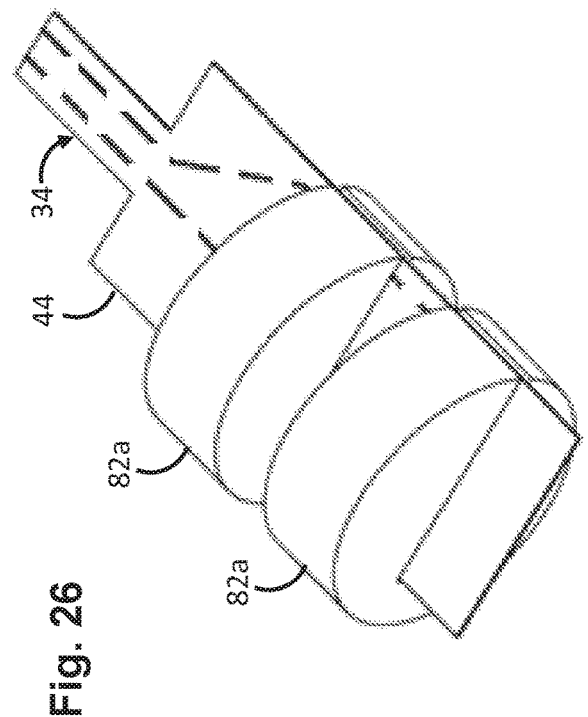
FIG. 26 is a perspective view of an assembly consisting of connector contacts of FIG. 25 affixed to the connector substrate portion of FIG. 24.
Figure 29:
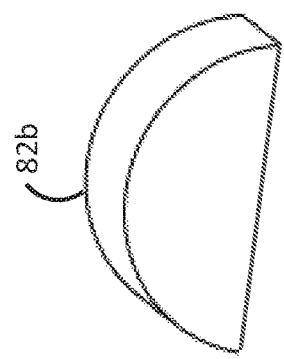
FIG. 29 is a perspective view of another embodiment of a rigid arcuate connector contact.

Each of the connector contacts 82*a* has an arc length that is greater than 180 degrees, and in the illustrated case, has an arc length nearly 360 degrees, resulting in disk-shaped connector contacts 82*a*. Each connector contact 82*a* comprises a notch 86 in which the connector substrate portion 44 is disposed. Preferably, the dimension of the notch 86 is roughly the same thickness of the connector substrate portion 44, so that the connector contacts 82*a* are firmly in contact with the respective connector pads 52. Thus, the connector contacts 82*a* can be slipped onto the connector substrate portion 44 into firm engagement with the respective connector pads 52, as illustrated in FIG. 26. An electrically conductive adhesive can be used to bond the connector contacts 82*a* to the respective connector pads 52 to enhance the structural and electrical contact between the connector contacts 82*a* and connector pads 52. The assembly of the connector substrate portion 44 and the connector contacts 82*a* can then be over-molded with electrically insulative material, such as, e.g., epoxy, silicone, polyurethane or other implantable polymeric material, which fills in the spaces between the connector contacts 82*a*, while leaving the arcuate outer surfaces of the connector contacts 82*a* exposed, to create the electrical insulator 84, as illustrated in FIG. 27.

Referring to FIGS. 28-31, another embodiment of a lead connector 18*c* is similar to the lead connector 18*b* described in FIGS. 24-27, with the exception that it comprises at least one rigid arcuate connector contact 82*b* (two shown) that has an arc length of 180 degrees or less. In this case, the connector contact 82*b* has an arc length of 180 degrees, resulting in a half-moon shaped connector contact 82*b*. As with the lead connector 18*b*, the arcuate surfaces of the connector contacts 82*a* preferably conform with the outer surface of the electrical insulator 84, such that the lead connector 18*b* has a smooth continuous outer surface that facilitates its insertion into the connector 32 of the neurostimulation device 30.

Figure 31:
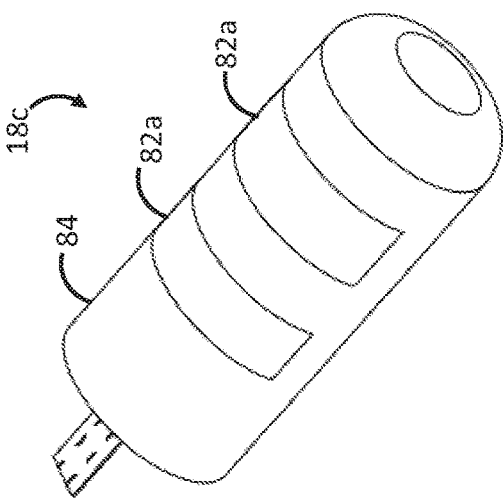
FIG. 31 is a perspective view of another embodiment of a lead connector of the electrode lead of FIG. 1 that can be formed from the assembly of FIG. 30.
Figure 28:
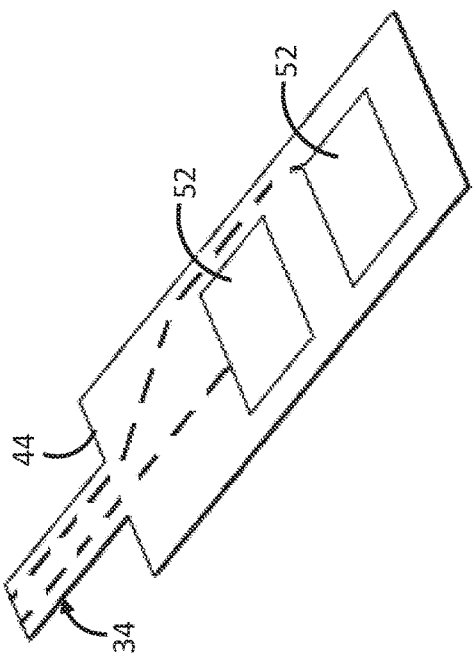
FIG. 28 is a perspective view of a connector substrate portion of the flexible circuit of FIG. 4.
Figure 30:
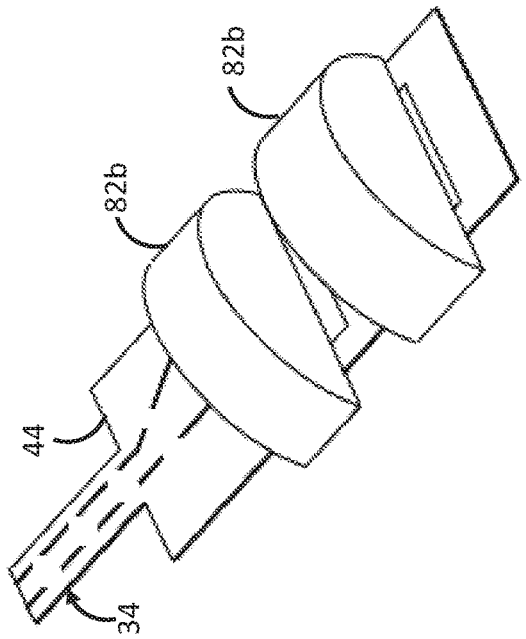
FIG. 30 is a perspective view of an assembly consisting of connector contacts of FIG. 29 affixed to the connector substrate portion of FIG. 28.

The connector contacts 82*b* can be bonded to the respective connector pads 52 using an electrically conductive adhesive, as illustrated in FIG. 30, and the assembly of the connector substrate portion 44 and the connector contacts 82*b* can be over-molded with electrically insulative material, such as, e.g., epoxy or polyurethane, which fills in the spaces between the connector contacts 82*b*, while leaving the arcuate outer surfaces of the connector contacts 82*b* exposed, to create the electrically insulator 84, as illustrated in FIG. 31.

Figure 32:
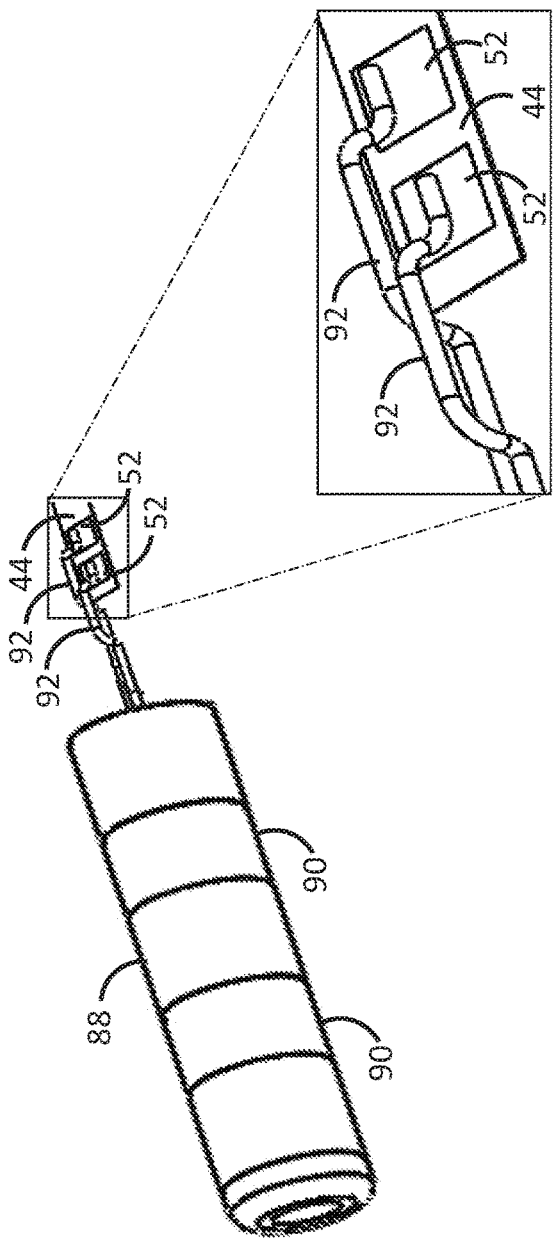
FIG. 32 is a perspective view of an assembly of a conventional cylindrical connector portion affixed to a connector substrate portion of the flexible circuit of FIG. 4.
Figure 33:
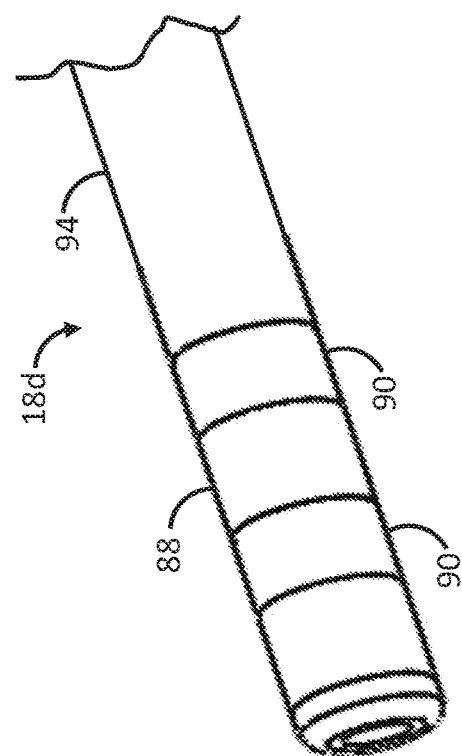
FIG. 33 is a perspective view of another embodiment of a lead connector of the electrode lead of FIG. 1 that can be formed from the assembly of FIG. 32.

Referring to FIGS. 32-33, still another embodiment of a lead connector 18*d* comprises the connector substrate portion 44 and connector pads 52 of the flexible circuit 34 described above, a cylindrical connector portion 88 having at least one connector contact 90 (two shown), at least one wire 92 (two shown) coupled between the connector pads 52 and the connector contact 90, and a cylindrical, rigid, electrical insulator 94 fully encapsulating the connector substrate portion 44. The cylindrical connector portion 88 may be a conventional in-line lead connector, and the connector contacts 90 are ring contacts that circumferentially extend around the cylindrical connector portion 88.

The wires 92, which may be included as part of the conventional cylindrical portion 88 may extend longitudinally along the cylindrical connector portion 88 from the respective connector contacts 90 out of the distal face of the cylindrical connector portion 88. The wires 92 extending from the cylindrical connector portion 88 can be wire-bonded to the respective connector pads 52 of the connector substrate portion 44, e.g., via soldering, welding, or otherwise an electrically conductive adhesive. As with the electrical insulator 84 described above with respect to the lead connector 18*a*, the electrical insulator 94 may be composed of a suitable material that can be over-molded over the connector substrate portion 44, such as, e.g., epoxy, silicone, or polyurethane, after the wires 92 from the cylindrical connector portion 88 have been wire-bonded to the respective connector pads 52. The outer surface of the electrical insulator 86 preferably conforms to the outer surface of the cylindrical connector portion 88, such that the lead connector 18*d* has a smooth continuous outer surface that facilitates its insertion into the connector 32 of the neurostimulation device 30.

Having described the structure and function of various embodiments of electrode leads 10, one method 100 of manufacturing electrode leads 10 will now be described with respect to FIG. 34. In this specific embodiment, multiple electrode leads 10 may be efficiently fabricated in parallel, although it should be appreciated that, in alternative embodiments, one electrode lead 10 may be fabricated at a time. First, two dielectric sheets (e.g., LCP sheets), i.e., a bottom dielectric sheet and a top dielectric sheet, are provided (step 102).

Next, sets of electrically conductive traces 48 for the multiple electrode leads 10 are disposed on the top surface of the bottom LCP sheets using a suitable process, such as semiconductor etching (step 104). For example, the sets of electrically conductive traces 48 can be disposed on the top surface of the bottom LCP sheet in a side-by-side relationship. The ends of these electrically conductive traces 48 will be enlarged to accommodate the formation of the connector pads 52 and electrode pads 54.

Next, windows 50 for the multiple electrode leads 10 are formed through the top LCP sheet (e.g., via cutting) at select locations (step 106), and LCP sheets are laminated together by, e.g., fusion bonding with heat and pressure, thereby forming the planar dielectric substrate 36 with embedded electrically conductive traces 48 (step 108). The windows 50 formed through the top LCP sheet expose portions of the embedded electrically conductive traces 48 to form connector pads 52 and electrode pads 54. The windows 50 may be cut, such that the connector pads 52 and electrode pads 54 are not embedded in the planar dielectric substrate 36, as illustrated in FIG. 8a, but preferably are cut in a manner, such that the electrode pads 54 are partially embedded in the planar dielectric substrate 36, as illustrated in FIG. 8b or 8c.

Next, the laminated LCP sheets are cut into the shapes of multiple planar dielectric substrates 36, each having a lead substrate portion 38, a connector substrate portion 44, a cuff substrate portion 46, and if existing, a branch lead substrate portion 38' (step 110). For example, the laminated LCP sheets may be in the shape of the flexible circuit 34 illustrated in FIG. 5, the flexible circuit illustrated in FIG. 14, the flexible circuit 34b illustrated in FIG. 18, or the flexible circuit illustrated in FIG. 20. In the case where the lead substrate portion 38 of the planar dielectric substrate 36 is sigmoid-shaped, as illustrated in FIG. 21h, the center portions of the dielectric sheets may be accordingly cut into a sigmoid shape.

Then, each of the planar dielectric substrates 36 is thermoformed into an appropriate three-dimensional shape (step 112). For example, the cuff substrate portion 46 of each dielectric plane substrate 36 may be thermoformed into a generally cylindrical shape with a desired diameter. In the case where the lead substrate portion 38 of the planar dielectric substrate 36 is helically-shaped, as illustrated in FIG. 21b, the lead substrate portion 38 may be appropriately thermoformed into this helical shape. For example, the lead substrate portion 38 may be wrapped around or bonded to a core and then thermoformed. In the case where the connector substrate portion 46 is affixed to the cylindrical rod 80, as illustrated in FIG. 23, the connector substrate portion 46 may be thermoformed into a generally cylindrical shape with a diameter equal to the diameter of the cylindrical rod 80. It should be appreciated that the thermoformed cuff substrate portion 46, lead substrate portion 38, and connector substrate portion 46 may be manipulated into other shapes, but will return to the shapes into which they were thermoformed in the absence of an external force.

Next, a pre-molded thin silicone sacrificial layer is disposed over the windows 50 (step 114). A colored pigment, such as a black pigment, can be used to highlight the molded silicone sacrificial layer. Then, elastic layers 64 are entirely disposed over top and bottom surfaces of the cuff substrate portion 46s of the planar dielectric substrates 36, e.g., by laminating or over-molding (step 116). Alternatively, the elastic layer 64 may be only disposed on the peripheral region of the cuff substrate portion, leaving the windows 50 inward from the peripheral region exposed.

Soft polymer tubings 70 may then be slid over the lead substrate portions 38 of the planar dielectric substrates 36 (step 118). A silicone tube of the appropriate dimensions can, for example, be immersed in heptane, which will cause the silicone tube 72 to swell and increase its diameter, making it possible to slide the expanding silicone tube 72 onto the lead substrate portion 38.

At this stage, the flexible circuit 34 (34a, 34b, or 34c) is complete. Lastly, lead connectors 18 are formed onto the connector substrate portions 44 of this flexible circuits 34 using suitable means to complete the lead electrode 10 (step 120). For example, in the case where the lead connector 18a illustrated in FIG. 23 is to be formed, the connector substrate portion 44 may be affixed around the cylindrical rod 80, such that the connector pads 52 face outwardly away from the cylindrical rod 80 to create the connector contacts 20. In the case where the lead connector 18b illustrated in FIG. 27 is to be formed, the connector contacts 82a can be slipped onto the connector substrate portion 44 via the notches 86, bonded to the connector contacts 82a to the respective connector pads 52 on the connector substrate portion 44, and over-molding the assembly with electrically insulative material to create the electrical insulator 84. In the case where the lead connector 18c illustrated in FIG. 31 is to be formed, the connector contacts 82b can be bonded to the connector substrate portion 44 in electrical contact with the respective connector pads 52 on the connector substrate portion 44, and the assembly can then be over-molded with electrically insulative material to create the electrical insulator 84. In the case where the lead connector 18d illustrated in FIG. 33 is to be formed, the wires 92 extending from the conventional cylindrical connector portion 88 are wire-bonded to the respective connector pads 52 of the connector substrate portion 44, and the connector substrate portion 44 is over-molded with electrically insulative material to create the electrical insulator 94.

Lastly, optional anti-inflammatory coatings 66 may be disposed over or within the elastic layers 64 on the cuff substrate portions 46 of the planar dielectric substrates 36 (step 122). It is desirable that the elastic layer 64 and optional anti-inflammatory coating 66 not cover the windows 50 that expose the connector pads 52 and electrode pads 54. Thus, the silicone sacrificial layer in the windows 50, along with the thin overmolded elastic layer 64 and optional inflammatory costing 66 directly over the windows 50, may then be removed (step 124). For example, under a microscope, using a scalpel blade and the pigmented color as a visual aid, the silicone sacrificial layer may be carefully removed out of the windows 50. Notably, since the silicone sacrificial layer is not bonded to the LCP, it can be easily peeled off.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An electrode lead, comprising:
   an elongated lead body having a proximal end and a distal end;
   a lead connector including a planar connector substrate disposed at a proximal end of the lead body, at least one connector pad carried by the connector substrate, a cylindrical connector portion having at least one connector contact, at least one wire respectively coupled between the at least one connector pad and the at least one connector contact, and a cylindrical, rigid, electrical insulator encapsulating the connector substrate;

an electrode carrying structure disposed at a distal end of the lead body;

at least one electrode contact carried by the electrode carrying structure; and at least one electrical conductor extending through the lead body between the at least one connector contact and the at least one electrode contact.

2. The electrode lead of claim 1, wherein each of the at least one connector contact is a ring contact.

3. The electrode lead of claim 1, wherein the at least one wire extends longitudinally along the cylindrical connector portion from the at least one connector contact out of a distal face of the cylindrical connector portion.

4. The electrode lead of claim 1, wherein the electrical insulator is composed of an epoxy or polyurethane.

5. The electrode lead of claim 1, wherein the lead body is planar.

6. The electrode lead of claim 1, wherein the electrode carrying structure is planar.

7. The electrode lead of claim 6, wherein the electrode carrying structure comprises a biologically compatible, elastic, electrically insulative cuff body affixed to the distal end of the lead body, the cuff body configured for being circumferentially disposed around a nerve, wherein the at least one electrode contact is affixed to the cuff body.

8. The electrode lead of claim 7, wherein the at least one electrode contact is configured for being on an inner surface of the cuff body when circumferentially disposed around a nerve.

9. The electrode lead of claim 6, wherein the electrode carrying structure comprises a biologically compatible, elastic, electrically insulative paddle body affixed to the distal end of the lead body.

10. The electrode lead of claim 1, further comprising an outer layer of insulative material composed of one of silicone, polyurethane, polyether polyurethane, polycarbonate polyurethane, parylene, perfluoroalkoxy alkanes (PFA), and polytetrafluoroethylene (PTFE).

11. The electrode lead of claim 1, wherein the connector substrate is a planar dielectric substrate.

12. The electrode lead of claim 11, wherein the planar dielectric substrate is composed of liquid crystal polymer (LCP).

13. The electrode lead of claim 11, wherein each of the at least one electrical conductor is an electrically conductive trace embedded within the planar dielectric substrate.

14. The electrode lead of claim 1, wherein the at least one electrode contact comprises three electrode contacts in a tripolar electrode arrangement.

15. The electrode lead of claim 1, wherein the lead connector is configured for being inserted into a corresponding connector of a neurostimulator.

\* \* \* \* \*